(12) United States Patent
Zhou et al.

(10) Patent No.: US 9,920,088 B2
(45) Date of Patent: Mar. 20, 2018

(54) TRITERPENE DERIVATIVE AND ITS ANTI-INFLUENZA USE

(71) Applicants: Peking University, Beijing (CN); University of Macau, Macau (CN)

(72) Inventors: Demin Zhou, Beijing (CN); Maorong Yu, Beijing (CN); Sulong Xiao, Beijing (CN); Fei Yu, Beijing (CN); Yiyun Peng, Beijing (CN); Yunyan Qiu, Beijing (CN); Lihe Zhang, Beijing (CN); Yitao Wang, Macau (CN)

(73) Assignee: University of Macao, Macao (CN)

( * ) Notice: Subject to any disclaimer, the term of this patent is extended or adjusted under 35 U.S.C. 154(b) by 106 days.

(21) Appl. No.: 14/437,611

(22) PCT Filed: Oct. 18, 2013

(86) PCT No.: PCT/CN2013/001266
§ 371 (c)(1),
(2) Date: Apr. 22, 2015

(87) PCT Pub. No.: WO2014/063441
PCT Pub. Date: May 1, 2014

(65) Prior Publication Data
US 2015/0274766 A1 Oct. 1, 2015

(30) Foreign Application Priority Data
Oct. 22, 2012 (CN) .......................... 2012 1 0402726

(51) Int. Cl.
| | |
|---|---|
| C07H 15/256 | (2006.01) |
| A61K 31/56 | (2006.01) |
| A61K 31/704 | (2006.01) |
| C07H 13/08 | (2006.01) |
| C07J 63/00 | (2006.01) |

(52) U.S. Cl.
CPC ........... *C07H 15/256* (2013.01); *A61K 31/56* (2013.01); *C07H 13/08* (2013.01); *C07J 63/008* (2013.01)

(58) Field of Classification Search
None
See application file for complete search history.

(56) References Cited

U.S. PATENT DOCUMENTS

| | | | | |
|---|---|---|---|---|
| 2010/0197898 A1* | 8/2010 | Guang | ................. | A61K 31/704 536/18.1 |
| 2014/0179780 A1* | 6/2014 | Rho | ....................... | A61K 36/48 514/557 |

FOREIGN PATENT DOCUMENTS

| | | |
|---|---|---|
| CN | 1438237 A | 8/2003 |
| CN | 101941996 A | 1/2011 |

OTHER PUBLICATIONS

"derivative" definition, Merriam-Webster OnLine dictionary, also available at http://www.merriam-webster.com/dictionary/derivative; last viewed Jul. 15, 2009.*
"prevent" definition, WordNet Search—3.0, also available at http://wordnet.princeton.edu; last viewed Nov. 14, 2007.*
Zhang, Li et al., Molecules, "Antioxidant, Anti-inflammatory and Anti-influenza properties of components from Chaenomeles speciosa", 2010, vol. 15, pp. 8507-8517.*
Assefa, H. et al., Bioorganic & Medicinal Chemistry Letters, 1999, vol. 9, pp. 1889-1894 (Year: 1999).*
Ashfaq, U.A. et al., Glycyrrhizin as antiviral agent against Hepatitis C Virus, J. Transl. Med., 9:112 (2011).
Cassels, B.K. and Asencio, M., Anti-HIV activity of natural triterpenoids and hemisynthetic derivatives 2004-2009, Phytochem Rev., 20 pages (2010).
Cichewicz, R.H. and Kouzi, S.A., Chemistry, biological activity, and chemotherapeutic potential of betulinic acid for the prevention and treatment of cancer and HIV infection, Med. Res. Rev., 24(1):90-114 (2004).
Das, K., Antivirals targeting influenza A virus, J. Med. Chem., 55(14):6263-77 (2012).
De Clercq, E., Highlights in the discovery of antiviral drugs: a personal retrospective, J. Med. Chem., 53(4):1438-50 (2010).
De L. E Silva, M. et al., Bioactive oleanane, lupane and ursane triterpene acid derivatives, Molecules, 17(10):12197-205 (2012).
International Search Report for PCT/CN2013/001266, 3 pages (dated Jan. 16, 2014).
Kazakova, O.B. and Tolstikov, G.A., Medical Prospects for Using Triterpenoids of Lupane Series, Chemistry for Sustainable Development, 16:717-720 (2008).
Mayaux, J.F. et al., Triterpene derivatives that block entry of human immunodeficiency virus type 1 into cells, Proc. Natl. Acad. Sci. USA, 91(9):3564-8 (1994).
Michaelis, M. et al., Glycyrrhizin exerts antioxidative effects in H5N1 influenza A virus-infected cells and inhibits virus replication and pro-inflammatory gene expression, PloS One, 6(5):e19705 (2011).
Osbourn, A. et al., The saponins: polar isoprenoids with important and diverse biological activities, Nat. Prod. Rep., 28(7):1261-8 (2011).
Pompei, R. et al., Glycyrrhizic acid inhibits virus growth and inactivates virus particles, Nature, 281(5733):689-90 (1979).
Song, G. et al., Discovery of the first series of small molecule H5N1 entry inhibitors, J. Med. Chem., 52(23):7368-71 (2009).
Sun, H. et al., Structure-activity relationships of oleanane- and ursanetype triterpenoids, Botanical Studies, 47: 339-368 (2006).

(Continued)

*Primary Examiner* — Layla D Berry
*Assistant Examiner* — Bahar Craigo
(74) *Attorney, Agent, or Firm* — Fox Rothschild LLP

(57) ABSTRACT

The present invention relates to the use of triterpenoid derivatives for the preparation of a medicament for preventing or treating influenza diseases, in which the substituents are as defined in the specification. The triterpenoid derivatives of the present invention have obvious inhibition effect on influenza virus, and are capable of obviously preventing influenza virus from entering cells, and can be used for preventing or treating influenza.

13 Claims, 3 Drawing Sheets

(56) References Cited

OTHER PUBLICATIONS

Tam, K.I. and Roner, M.R., Characterization of in vivo anti-rotavirus activities of saponin extracts from Quillaja saponaria Molina, Antiviral. Res., 90(3):231-41 (2011).

Utsunomiya, T. et al., Glycyrrhizin, an active component of licorice roots, reduces morbidity and mortality of mice infected with lethal doses of influenza virus, Antimicrob. Agents Chemother., 41(3):551-6 (1997).

Vanderlinden, E. et al., Novel inhibitors of influenza virus fusion: structure-activity relationship and interaction with the viral hemagglutinin, J. Virol., 84(9):4277-88 (2010).

Wolkerstorfer, A. et al., Glycyrrhizin inhibits influenza A virus uptake into the cell, Antiviral Res., 83(2):171-8 (2009).

Written Opinion for PCT/CN2013/001266, 4 pages (dated Jan. 16, 2014).

Wang, H., et al., Elucidation of the pharmacophore of echinocystic acid as a new lead for blocking HCV entry, European J. Med. Chem., 64: 160-168 (2013).

Yu, F. et al., Development of Oleanane-Type Triterpenes as a New Class of HCV Entry Inhibitors, Journal of Medicinal Chemistry, 56: 4300-4319 (2013).

\* cited by examiner

Virus hemagglutination potency determination $2^{-1}$ $2^{-2}$ $2^{-3}$ $2^{-4}$ $2^{-5}$ $2^{-6}$ $2^{-7}$ $2^{-8}$ $2^{-9}$ $2^{-10}$ $2^{-11}$ 0

Q9 — 16.7 5.6 1.9 0.6 DMSO (μM)
containing virus
not containing virus

HA antibody
containing virus
not containing virus

TRITERPENE DERIVATIVE AND ITS ANTI-INFLUENZA USE

TECHNICAL FIELD

The present invention relates to a new use of triterpene derivatives, i.e. the use of triterpene derivatives for the prevention or treatment of influenza in particular influenza A.

BACKGROUND ART

Influenza is an acute, infectious respiratory system disease caused by influenza viruses. According to the difference in antigen of internal nucleoprotein (NP) and matrix protein (M), influenza viruses can be classified into influenza A, B and C viruses. Pandemic of influenza A virus can cause high morbidity and mortality and a serious threat to human health (W.H.O. 2003; Coleman 2007). In the twentieth century, influenza A viruses mainly caused three major flu, i.e. H1N1 in 1918, H2N2 in 1957, and H3N2 in 1968, and killed about 50 million people (Kilbourne 2006; Taubenberger, Hultin et al. 2007). Influenza A in 2009 was also caused by H1N1 influenza virus (Dawood, Jain et al. 2009; Zimmer and Burke 2009), which spread rapidly and attracted the attention of the world. According to statistics, about 300-500 thousands of people worldwide died annually from influenza (Fiore, Shay et al. 2007).

Up to now, FDA-approved anti-influenza drugs mainly include two categories. The first category includes Tamiflu (Oseltamivir) and Relenza (zanamivir), which mainly inhibit influenza virus neuraminidase (NA), blocking the release of influenza virus from infected cells (Palese 2004; De Clercq 2006). The second category includes amantadine and rimantadine, which mainly destroy influenza virus M2 protein ion channel activity and inhibit the uncoating process of influenza virus (Jing, Ma et al. 2008). However, US Centers for Disease Control and Prevention has found in sample survey that in the strains of H3N2 in 2008/2009 and pandemic H1N1 virus in 2009, 100% of the strains were resistant to adamantane drugs; 99.6% of the seasonal H1N1 Influenza viruses were resistant to Tamiflu (http://www.cdc.gov/flu/weekly/weeklyarchives2008-2009/weekly35.htm).

Triterpenoids are a class of natural compounds widely found in nature, and its structure includes five rings of A, B, C, D, E and 30 carbon atoms (Hostettmann, K et al. 1995; Waller, G. R. et al. 1996). Triterpenoids caused more and more attention due to various biological and pharmacological activities. For example, betulinic acid and its derivatives have been used as anti-tumor and anti-HIV drugs in clinical trials (U.S. Pat. Nos. 5,679,828; 6,689,767; 6,369,109; U.S. App. Pub. No. 2004/0204389); oleanolic acid is an active ingredient for protecting the liver against chemical damage and controlling HIV infection (Liu, J. et al. 2005); moreover, European researchers recently reported that hawthorn acid can inhibit spread of HIV in the body, with an inhibition rate up to 80%. The prior application 201110373224.3 filed by the patent applicant, which has not been disclosed at present, discloses a class of triterpene derivatives and their use for the prevention and treatment of viral hepatitis, not for the prevention and treatment of influenza. The inhibition of triterpenoids on influenza virus has not been reported.

SUMMARY OF THE INVENTION

An object of the present invention is to provide triterpenoids, stereoisomers thereof, epimers thereof, configurational isomers thereof or pharmaceutically acceptable salts thereof or hydrates thereof, which can inhibit the infection of influenza viruses in particular influenza A virus.

Another object of the invention is to provide methods for preparing the triterpene and derivatives thereof or pharmaceutically acceptable salts or hydrates thereof.

Another object of the invention is to provide use of the triterpene derivatives or pharmaceutically acceptable salts or hydrates thereof for the prevention or treatment of influenza preferably influenza A.

The object of the invention is achieved by following embodiments.

The invention in one aspect provides a series of compounds such as the following structural formula, stereoisomers thereof, epimers thereof, configurational isomers thereof, or pharmaceutically acceptable salts thereof or hydrates thereof, and their use for the preparation of a medicament for the prevention or treatment of influenza especially influenza A in patients including human and animals) in need of such treatment.

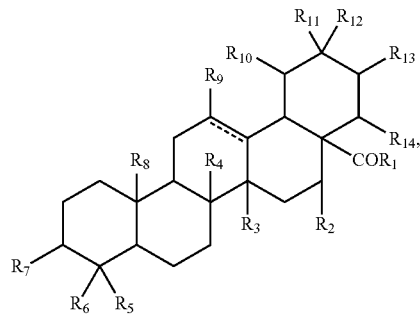

wherein
dotted line represents optional, i.e., single or double bond; R1 is XR1', wherein X is O or NH, R1' is hydrogen, monosaccharides, oligosaccharides, polysaccharides or derivatives thereof, or vitamin C, sialic acid, amino sugar (one, two, three sugar), Tamiflu and prodrugs thereof; "the derivatives of monosaccharides, oligosaccharides, polysaccharides" refers to that one or more such as 2, 3 or 4 hydroxy groups thereof can be substituted by substituents such as C1-C6 alkanoyloxy group, C1-C6 alkoxy, benzoyloxy, and/or benzyloxy, and the like (e.g., the hydrogen atom of the benzene ring may be substituted with one or more halogen, nitro, amino and/or C1-C6 alkyl groups); one of the hydroxyl groups can be substituted by hydrogen, amino group or an acetylamino group;

R2 and R7 are each independently selected from the group consisting of H, halogen, hydroxy, cyano, nitro, mercapto, carbonyl, C1-C6 thioalkyl, C1-C6 alkyl group unsubstituted or substituted by a hydroxyl group, an amino group or a carboxyl group, amino, NR11'R12', wherein R11' and R12' are each independently selected from C1-C6 alkyl group unsubstituted or substituted by a hydroxyl group, an amino group or a carboxyl group;

R3, R4, R5, R6 and R8 are each independently selected from the group consisting of H, C1-C6 alkyl group unsubstituted or substituted by a hydroxyl group, an amino group or a carboxyl group;

R9 is selected from the group consisting of H, halogen, hydroxy, cyano, nitro, mercapto, C1-C6 thioalkyl group, a carbonyl group, an oxime group, C1-C6 alkyl group unsubstituted or substituted by a hydroxyl group, an amino group or a carboxyl group;

R10, R11, R12, R13 and R14 are each independently selected from the group consisting of H, OH, NHR9' (wherein R9' is H, C1-C3 alkyl group unsubstituted or substituted by hydroxyl, amino or carboxyl group), mercapto, C1-C6 thioalkyl, C1-C3 alkyl unsubstituted or substituted by hydroxyl, amino or carboxyl;

provided that when R7 is hydroxyl, R2 and R1' are not hydrogen,

According to one embodiment of the invention, wherein R10, R11, R12, R13, and R14 are each independently selected from the group consisting of H, hydroxy, amino, C1-C3 alkyl group, preferably methyl group, unsubstituted or substituted by hydroxy, amino or carboxyl group.

According to another embodiment of the invention, wherein R10, R11, R12, R13 and R14 are each independently selected from the group consisting of H, hydroxy, amino or methyl; preferably R11 and R12 are each independently selected from H or methyl, R10 is H, and/or R13 and R14 are each independently selected from H, OH or NH2.

According to another embodiment of the invention, wherein the drug is administered by oral, rectal, nasal, aerosol or particulate inhalation, or administered locally by buccal and sublingual, transdermal, vaginal, intravesical, intralesional and parenteral route; sprays are preferred for oral or nasal spray administration or indoor or local environment sterilization and disinfection.

According to another embodiment of the invention, wherein the monosaccharide is independently selected from the group consisting of glucose, mannose, fructose, xylose, arabinose, galactose, ribose or deoxyribose, wherein the oligosaccharide is maltose, sucrose or lactose, or wherein the derivative means that one, two, three or four hydroxy groups of "monosaccharides, oligosaccharides, polysaccharides" are substituted by C1-C4 alkanoyloxy, C1-C4 alkoxy, benzoyloxy and/or benzyloxy group; or one hydroxy group thereof is substituted by hydrogen, amino or acetylamino group; preferably one hydroxy group, or two, three or four hydroxy groups of "monosaccharides, oligosaccharides, polysaccharides" are substituted by acetoxy, benzyloxy, methoxy and/or benzoyloxy; or one hydroxy group of "monosaccharides, oligosaccharides, polysaccharides" is substituted by hydrogen, amino group or acetylamino group.

According to another embodiment of the invention, wherein the saccharide is an amino sugar, e.g., neamine, neomycin, kanamycin or gentamicin.

According to another embodiment of the invention, wherein the X is O or NH, the sugar is a monosaccharide or disaccharide, or an acetylated derivative in which the hydroxy group of monosaccharide or disaccharide is substituted by acetoxy group.

According to another embodiment of the invention, wherein R2 is independently selected from the group consisting of H, OH, carbonyl, SH or NH2, preferably H, OH or carbonyl group.

According to another embodiment of the invention, wherein R3, R4, R5, R6 and R8 are each independently selected from methyl.

According to another embodiment of the invention, wherein R7 is independently selected from the group consisting of H, OH, carbonyl, NH2 or SH, preferably OH or carbonyl group.

According to another embodiment of the invention, wherein the compounds are

Echinocystic acid,

3β,16α-dihydroxy-olean-12-en-28-oic acid-28-O-(2,3,4,6-tetra-O-acetyl-β-D-glucoside), 3β,16α-dihydroxy-olean-12-en-28-oic acid-28-O-(β-D-glucoside), 3β,16α-dihydroxy-olean-12-en-28-oic acid-28-O-(2,3,4-tri-O-acetyl-β-D-xyloside), 3β,16α-dihydroxy-olean-12-en-28-oic acid-28-O-(β-D-galactoside), 3β,16α-dihydroxy-olean-12-en-28-oic acid-28-O-(β-D-lactoside), 3β,16α-dihydroxy-olean-12-en-28-oic acid-28-O-(hepta-O-acetyl-β-D-maltoside), 3β,16α-dihydroxy-olean-12-en-28-oic acid-28-N-(2,3,4,6-tetra-O-acetyl-β-D-galactoside), 3β,16α-dihydroxy-olean-12-en-28-oic acid-28-N-(β-D-galactoside), 3,16-dione-olean-12-en-28-oic acid-28-N-(2,3,4,6-tetra-O-acetyl-β-D-galactoside), 3,16-dione-olean-12-en-28-oic acid-28-N-(β-D-galactoside), 3β-hydroxy-olean-12-en-28-oic acid-28-N-(2,3,4,6-tetra-O-acetyl-β-D-galactoside), 3β-hydroxy-olean-12-en-28-oic acid-28-N-(β-D-galactoside), 3β-hydroxy-olean-12-en-28-oic acid-28-N-(2,3,4,6-tetra-O-acetyl-β-D-mannoside), or 3β-hydroxy-olean-12-en-28-oic acid-28-N-(β-D-galactoside).

When containing a chiral atom, above compounds include R and S configurations and mixtures thereof.

The sugar moieties of the above derivatives also include the epimers of the sugar.

The invention also provides the triterpene derivatives described above, which do not include compounds known in the art, e.g. echinocystic acid.

The invention further provides a method for preparing the triterpene derivatives, as described in the following preparation method of compounds according to the invention.

Meanwhile, the invention provides the use of the triterpene derivatives according to the present invention for prevention or treatment of influenza in particular influenza A.

Moreover, the invention provides an inhibitor for inhibiting influenza virus infection, in particular for inhibiting the entry of influenza virus into a host cell, wherein the inhibitor includes triterpene derivatives described above.

Further, the invention provides a medicament for preventing or treating influenza, which contains triterpene derivatives described above.

Furthermore, the invention provides a method for preventing or treating influenza in particular influenza A, the method comprising triterpene derivatives administering to human or other mammals.

BRIEF DESCRIPTION OF FIGURES

FIG. 3: Hemagglutination inhibition assay to verify whether Q9 affects the binding of influenza virus to cell receptor. Red blood cells are agglutinated by influenza virus (WSN strain) hemagglutinin protein (HA), without red dot being observed. HA mediates the entry of influenza viruses into the cells. Anti-HA antibody was used as a positive control in this experiment. DMSO was used as a negative control. The amount of virus ($2^5$ dilution), and each well was added 50 ul 1% chicken erythrocytes.

FIG. 4: Pseudotype virus experiments to detect the inhibitory effect of Q9 on H1N1 and H5N1 pseudotype viruses. Pseudotype virus consists of core protein of HIV and envelope protein HA/NA of influenza viruses. Two subtypes of influenza viruses, i.e. H1N1 and H5N1 pseudotype viruses, were inhibited by Q9; the concentration of Q9 was 50 µM. The inhibition rate of DMSO as a negative control was set to zero.

FIG. 5: Cytotoxicity of compounds on MDCK cells at a concentration of 50 µM. DMSO was taken as a negative control. Canine kidney epithelial cells (MDCK) were passaged and incubated for 24 h, the drug was added to the DMEM medium, mixed well and added to MDCK cells, in 48 h the cell viability was assayed using Celltiter-Glo test kit.

EMBODIMENTS

Definition

Figure 1:
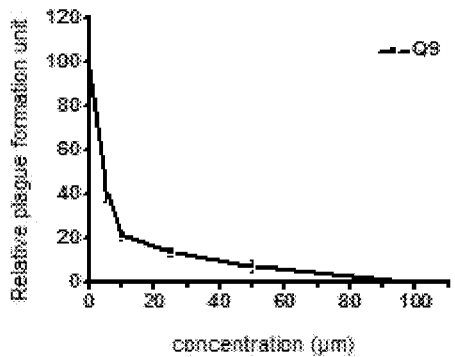
FIG. 1: A chart of the inhibition effect of Q9 on influenza virus verified by plaque formation inhibition assays. Ordinate shows the numbers of plaques formed; abscissa shows the concentrations of the compound.
Figure 2:
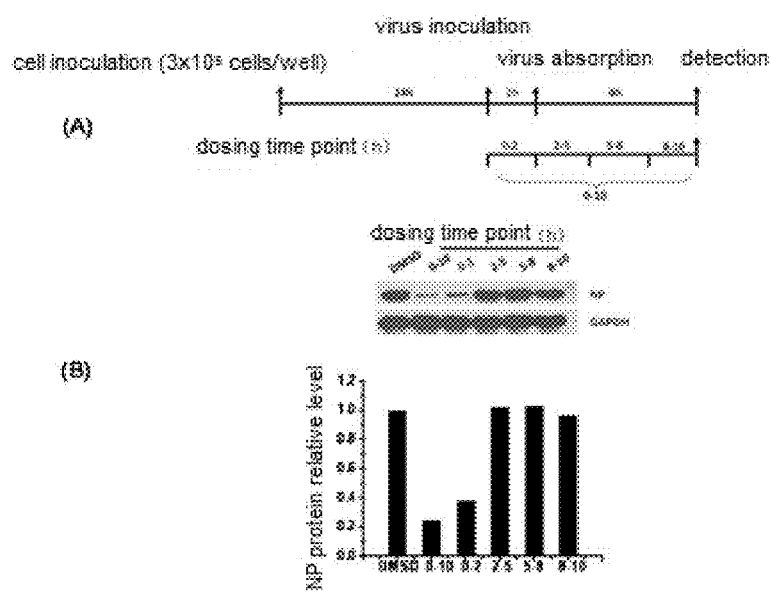
FIG. 2: Time-of-addition experiments to identify which step of viral replication Q9 targets. (A) Diagram of time-of-addition experiments. MDCK cells were infected with WSN virus (MOI=1.5), and 50 μM of Q9 was added in 0-10, 0-2, 2-5, 5-8 or 8-10 h after infection. Cell lysates were harvested at 10 h after infection and applied to Western blotting for replication analysis. (B) Western blotting results of time-of-addition experiment. GAPDH was used as internal reference of cells, NP as a marker for the detection of influenza viruses.
Figure 6:
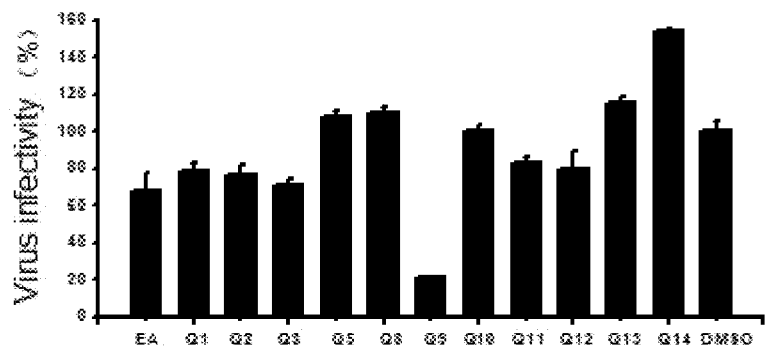
FIG. 6: The antiviral activity of compounds against influenza viruses at 50 µM. DMSO was taken as a negative control. After the canine kidney epithelial cells (MDCK) passaged and incubated for 24 h, the WSN virus (MOI=1) and the compound to be tested were added to DMEM, mixed well and then added to MDCK cells, in 48 h the cell viability was detected using Celltiter-Glo test kit. Infectivity rate=100%-protection rate of a compound against cytopathic effect. The protection rate of compound against cytopathic effect=100%×(1−(Test compound-Median Virus 1)/(Median Cells-Median Virus2)). Wherein Test compound represents the cell viability of the group in which only the compound to be tested was added, without virus; Median Virus1 represents the cell viability of the group in which the compound to be tested and virus group were added; Median Cells represent the cell viability of the group in which only 1% DMSO was added; Median Virus2 represents the cell viability of the group in which 1% DMSO and virus were added.
Figure 7:
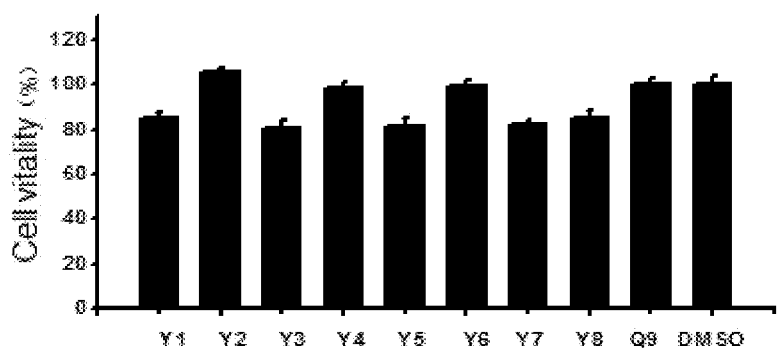
FIG. 7: Cytotoxicity test of compounds on MDCK cells at a concentration of 50 µM The method was as described in FIG. 5.
Figure 8:
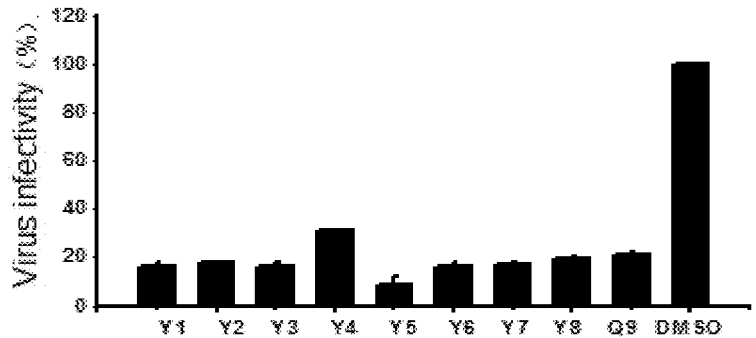
FIG. 8: The antiviral activity of compounds against influenza virus at 50 µM. The method was as described in FIG. 6.

The term "C1-C4 alkyl" refers to an alkyl containing 1-4 carbon atoms, such as methyl, ethyl, propyl, isopropyl, n-butyl, isobutyl, t-butyl.

The term "C1-C6 alkyl" refers to straight or branched chain alkyl group containing 1-6 carbon atoms, such as methyl, ethyl, propyl, isopropyl, n-butyl, isobutyl, tert-butyl group, pentyl or hexyl and so on.

The term "monosaccharide" refers to sugars that cannot be hydrolyzed into simpler polyhydroxy aldehydes or polyhydroxy ketones. Monosaccharide has a general formula of $C_nH_{2n}O_n$. According to the number of carbon atoms contained in the molecule, monosaccharide is divided into triose, tetrose, pentose and hexose, etc. The monosaccharide having a structure of polyhydroxy aldehyde is called aldose (e.g. ribose is aldopentoses; glucose and galactose are aldohexose), the monosaccharide having a structure of polyhydroxy ketones is called as ketose (e.g. fructose and sorbose are hexyl ketose). The most important monosaccharides are glucose and fructose. Monosaccharides are mainly present in the form of cyclic hemiketal sugar structure (oxygen cyclic structure), e.g., ribose, arabinose, xylose, ribulose, glucose, fructose, and galactose.

The term "oligosaccharide" refers to sugars formed by condensation and dehydration of 2-9 same or different monosaccharide molecules, such as maltose, sucrose or lactose.

The term "polysaccharide" refers to sugars formed by condensation and dehydration of more than ten same or different monosaccharide molecules, such as starch, cyclodextrin and the like.

The term "derivatives of monosaccharide, oligosaccharide, polysaccharide" refers to that one or more such as 2, 3 or 4 hydroxy groups thereof can be substituted by substituents such as C1-C6 alkanoyloxy group, C1-C6 alkoxy, benzoyloxy, and/or benzyloxy, and the like (e.g., the benzene ring may be substituted with one or more halogen, nitro, amino and/or C1-C6 alkyl groups); one of the hydroxy groups thereof can be substituted by hydrogen, amino group or an acetylamino group;

The term "amino saccharides" refers to mono-, oligo- or polysaccharides in which one or more hydroxy groups of the sugars are substituted by amino group, e.g., neamine, streptomycin, kanamycin, neomycin or gentamycin.

The term "triterpenoids" refers to a substance formed by connecting hydroxy-removed isoprenes end to end, the majority of them are terpenoids containing 30 carbon atoms, and a small part of them are terpenoids containing 27 carbon atoms, e.g., oleanolic acid, echinocystic acid, and the like.

The term "halogen" refers to fluoro, chloro, bromo or iodo.

The term "C1-C6 thioalkyl" refers to C1-C6 alkyl in which one hydrogen atom is substituted with a sulfur atom.

The term "C1-C6 alkoxy" refers to a group formed by connecting C1-C6 alkyl with an oxygen atom, such as methoxy, ethoxy, hexyloxy.

The term "C1-C6 alkanoyloxy" refers to a group formed by connecting C1-C6 alkyl with acyloxy group, such as acetoxy.

Preparation method of the compounds according to the invention

In another aspect, the invention provides methods for preparing the above compounds.

The triterpene compounds and derivatives according to the invention can be extracted from natural plants, and/or prepared by chemical synthesis or semi-synthesis or chemical structure modification. In one embodiment of the invention, some of triterpenoids may be extracted from plants or commercially available, and other triterpenoids can be prepared by structural modification or chemical synthesis or semi-synthesis of the above triterpenoids.

The extraction method comprises dipping triterpenoid-rich plants in a polar solvent at reflux, filtering to remove insolubles, concentrating, subjected to acid treatment, and purifying on silica gel chromatographic column (e.g., dichloromethane/methanol gradient elution) to separate triterpene aglycone.

A series of naturally occurring triterpenoid sapogenins were extracted by those skilled in the art through conventional methods, for example, oleanolic acid, betulinic acid, echinocystic acid (EA), etc., which are commercially available and can be used as starting materials for the synthesis of the derivatives of the invention.

Semi-synthetic method of some derivatives comprises protecting the hydroxyl group of triterpenoid aglycone with a protecting group, activating the carboxyl (such as forming acyl chloride, ester or anhydride), coupling with a sugar or amino sugar, and deprotecting to form triterpenoid saponins.

Pharmaceutically acceptable salts or hydrates of triterpenoids can be prepared by conventional techniques in the art.

The compounds according to the invention can be prepared by the method described in the specification of Chinese patent application No. 201110373224.3, the entire contents of this application is hereby fully incorporated herein by reference. For example, the compounds according to the invention are prepared by general synthesis processes and examples as well as similar processes described below.

General Synthesis Processes

The variety of triterpenoids according to the invention can be prepared by different reactions.

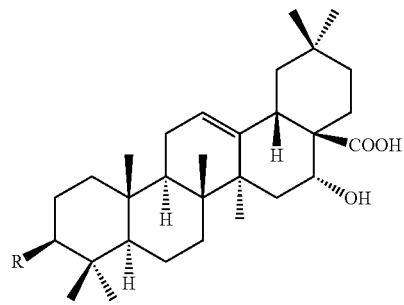

R = OH, OCH3, OTs, NH2, OTBDMS, OAc, = O

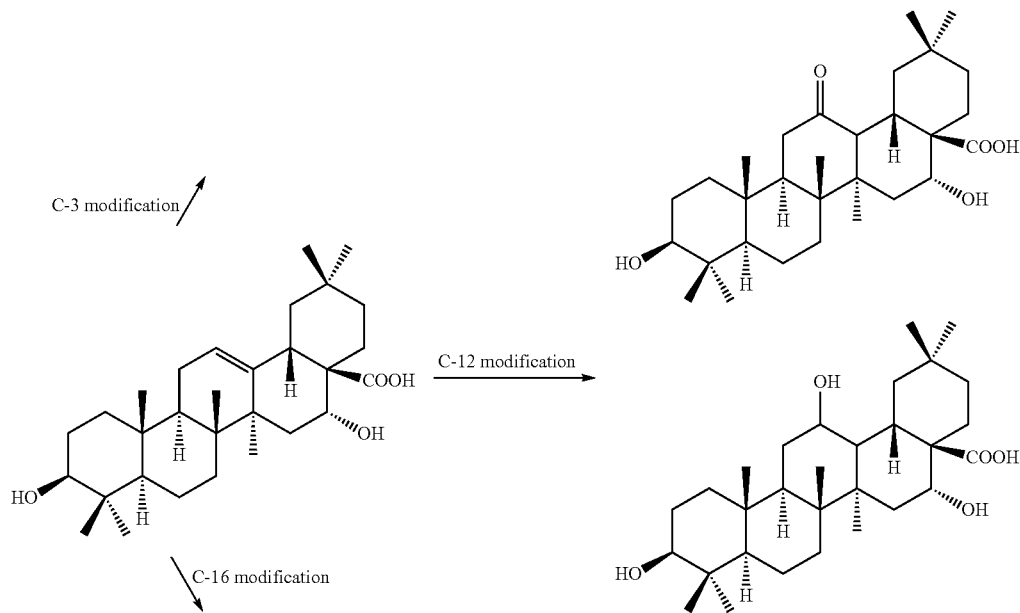

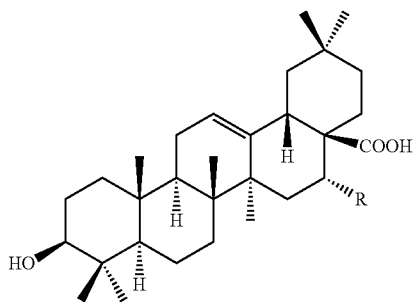

R = OH, OCH3, OTs, NH2, OTBDMS, OAc, = O

Connection of EA with Sugar

α-D-glucopyranose is taken as an example, and the synthesis route is described as follows:

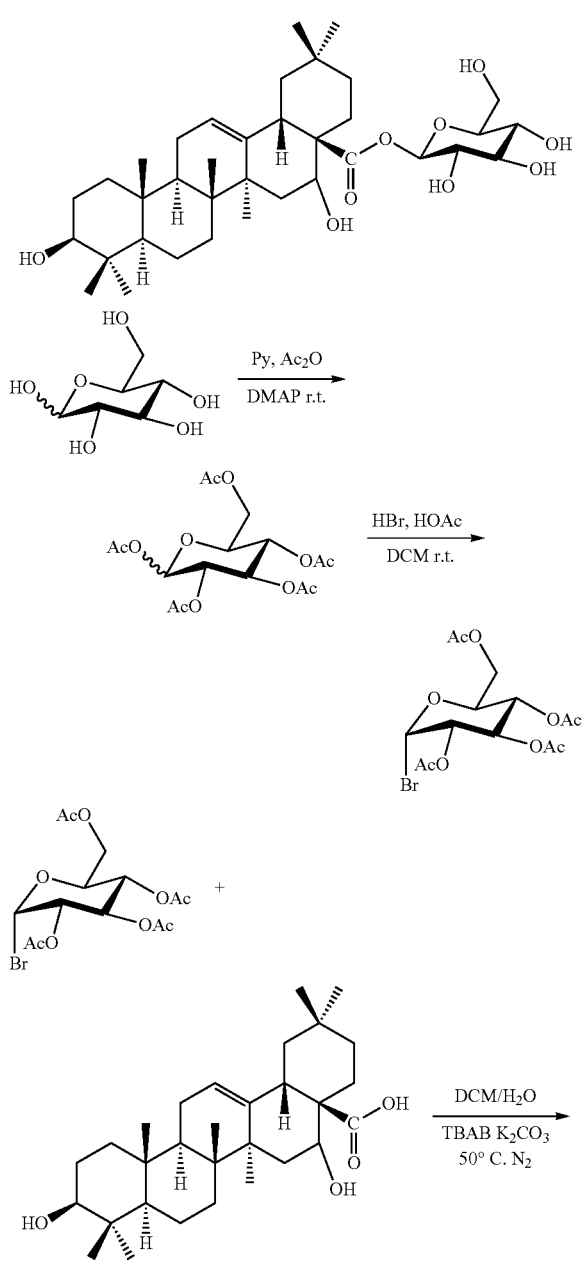

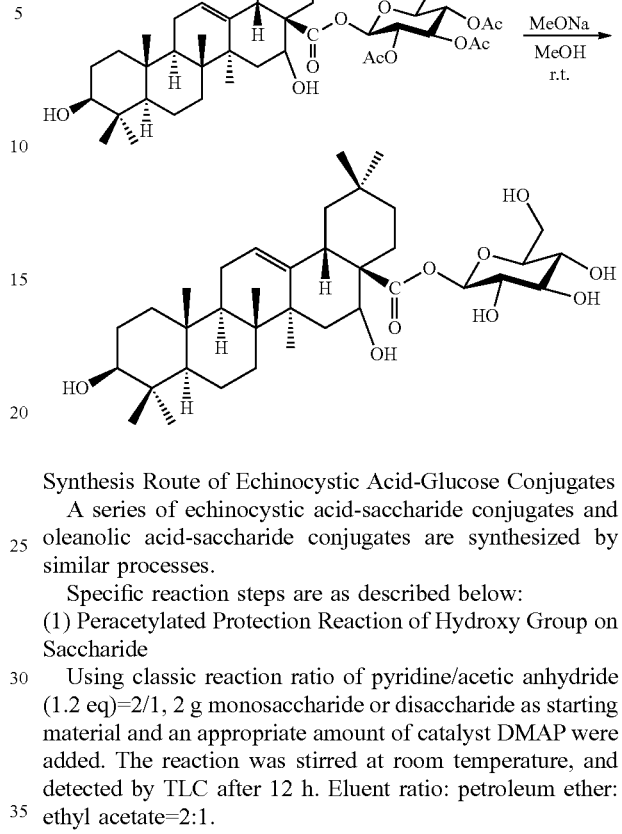

Synthesis Route of Echinocystic Acid-Glucose Conjugates

A series of echinocystic acid-saccharide conjugates and oleanolic acid-saccharide conjugates are synthesized by similar processes.

Specific reaction steps are as described below:

(1) Peracetylated Protection Reaction of Hydroxy Group on Saccharide

Using classic reaction ratio of pyridine/acetic anhydride (1.2 eq)=2/1, 2 g monosaccharide or disaccharide as starting material and an appropriate amount of catalyst DMAP were added. The reaction was stirred at room temperature, and detected by TLC after 12 h. Eluent ratio: petroleum ether: ethyl acetate=2:1.

Post-treatment: the resultant was subjected to rotary evaporation to remove pyridine, dissolved with dichloromethane, washed with 1N HCl solution, dried over $MgSO_4$, the solvent was removed by evaporation, with a yield of 95-98%, set aside.

The crude product was introduced directly into the next reaction without purification, but it was necessary to ensure single product point on thin layer. If the product point was not single, the product was necessarily subjected to purification by column chromatography.

(2) Preparation of Bromo Sugar Donor 1 mmol of peracetylation protected sugar was dissolved in dichloromethane, added dropwise with 2 eq HBr-HOAc solution in ice bath, the temperature was elevated to room temperature after 1 h, and the reaction was allowed for 13 h.

Post-treatment: The resultant was washed with an appropriate amount of water, and then washed with saturated $NaHCO_3$ solution, followed by subjected to next reaction without drying.

(3) Glycosylation of Echinocystic Acid

Phase transfer catalysis reaction was employed in this reaction. The glycosyl donor obtained in above step reaction, which was not subjected to drying and isolation, was dissolved with 20 mL of dichloromethane, added with 188.8 mg echinocystic acid (EA), 138 mg $K_2CO_3$, 51.52 mg tetra-n-butylammonium bromide, 2 mL of water. The reaction was allowed at 50° C. with reflux under $N_2$ protection. After 12 h, the reaction was stopped.

Post-treatment: the reaction solution was washed with 10 mL water once, dried over $MgSO_4$, and then purified on chromatographic column.

This reaction was mild in reaction condition, simple in post-treatment, and high in yield.

In this reaction, although the glycosyl donor is different, the reaction produced a by-product with a polarity of less than EA, which can be removed by conventional separation method.

(4) High Selective Deacetylation of Intermediate Products

The reactant was dissolved in an appropriate amount of MeOH, added with an appropriate amount of MeONa, allowed to react at room temperature. The reaction process was detected by TLC. Generally, the reaction was completed in an hour.

Post-treatment: a cation exchange resin was added. The pH was adjusted to neutral. The resin was filtered off. The filtrate was subjected to rotary evaporation to remove solvent, and then purified on chromatographic column.

Synthesis of the Derivatives of 12-Ketone/Hydroxy Group

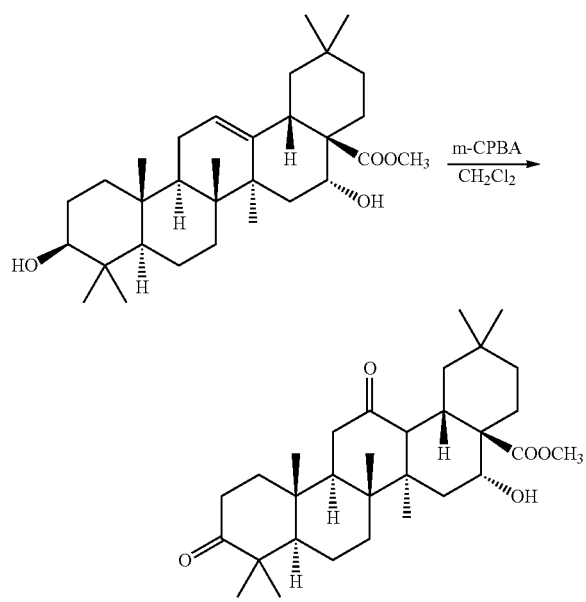

328 mg of echinocystic acid methyl ester was dissolved in 10 ml of dichloromethane, added with 92 mg of m-CPBA (m-chloroperoxybenzoic acid). The reaction was allowed at room temperature overnight, and then subjected to column separation to give 260 mg of white solid, with a yield of 77%.

Synthesis of 12-Hydroxy-Echinocystic Acid

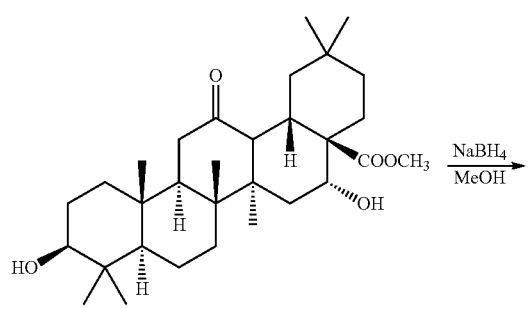

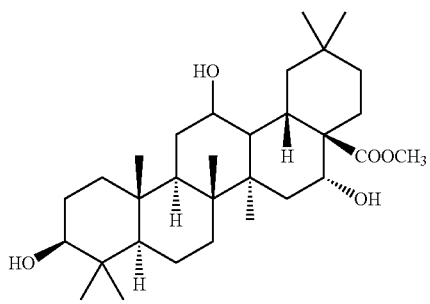

150 mg of the above compound was dissolved in 5 ml of methanol in an ice bath, added with 36 mg of sodium borohydride, allowed to react overnight. Treatment method: most of the solvent was evaporated off, extracted with water, added with 3 ml of 1 M HCl, extracted three times with ethyl acetate, collected, evaporated, purified with petroleum ether/ethyl acetate=2:1 on chromatographic column to give 122 mg of white solid, with 75% yield.

Modification of 3-Hydroxy Group

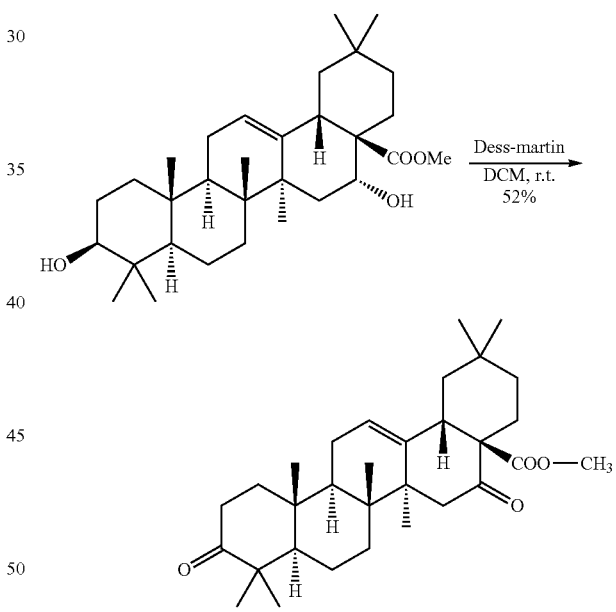

Synthesis of 3,16-Dione

To 25 mL round bottom flask was added 120 mg of EA methyl ester, 200 mg of anhydrous sodium bicarbonate and 410 mg of Dess-martin oxidant, allowed to react at room temperature in dichloromethane solvent for 48 hours. The reaction system was milky white suspension. The resultant was filtered, the solvent was removed by reduced pressure evaporation. The resulting solid was isolated and purified on chromatographic column with an eluent: petroleum ether: ethyl acetate=3:1 to give 62 mg of a white solid EA methyl ester-dione, with 52% yield.

Synthesis of 3-Amino Group

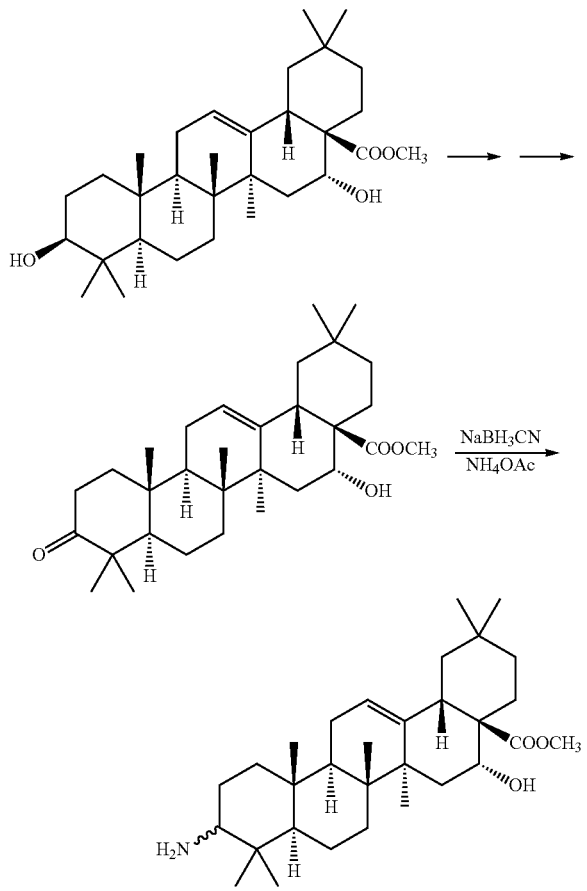

Echinocystic acid methyl ester was synthesized to 3-keto echinocystic acid methyl ester. 240 mg of echinocystic acid was dissolved in 3 ml of dichloromethane, added with 4 ml of methanol, added with 150 mg of ammonium acetate in an oil bath at 60° C., allowed to reaction for 1 h, cooled, added with 20 mg of NaBH$_3$CN (sodium cyanoborohydride), allowed to react for 24 h. Post-treatment: most of the solvent was evaporated off, extracted with 10 ml of water and 10 ml of ethyl acetate three times. The ester layer was collected and purified on chromatographic column. The column was washed with petroleum ether/ethyl acetate=1:1, and then eluted with dichloromethane/methanol=8.5:1 to give 168 mg of white solid, with 70% yield.

Other triterpenoids derivatives can be prepared by the person skilled in the art.

The activity of the compounds according to the invention

The compounds of the invention have the activity against influenza viruses, can be used for the prevention or treatment of human or animal influenza, particularly influenza A.

The compounds of the invention can prevent the entry of influenza virus into cells, but are not limited to this mechanism.

The compounds of the invention can be administered in the form of pure compounds or a mixture of compounds, or preferably administered in a pharmaceutical excipient, diluent or carrier.

Active agents may be administered by any suitable route for the treatment of disorders.

Suitable administration routes include: oral, rectal, nasal, aerosol or particulate inhalant, topical (including buccal and sublingual), transdermal, vaginal, intravesical, intralesional and parenteral (including subcutaneous, intramuscular, intravenous, sternum, intrathecal, epidural and intradermal). The compounds of the invention are particularly suitable as sprays for buccal or nasal spray administration or for indoor or local environment sterilization and disinfection.

The present invention also relates to a composition comprising a compound of the present invention together with one or more pharmaceutically acceptable additives and optionally other drugs. Pharmaceutically acceptable additives may be a carrier, diluent, adjuvant and/or an excipient, including all conventional solvents, dispersion agents, fillers, solid carriers, coating agents, antifungal or antibacterial agents, transdermal permeating agents, surfactants, isotonic agents and the absorbent, and slow or controlled release matrix. The active agent may be in the form of kit suitable for simultaneous, separate or continuous administration of the component of the active agent. In the sense of compatible with other ingredients of the composition and patient physiologically tolerable, each carrier, diluent, adjuvant and/or excipient must be "pharmaceutically acceptable". The composition may be conveniently presented in unit dosage form and can be prepared by processes well known in the field of pharmaceutical preparation. Such processes comprise the step of: mixing active ingredient with a carrier, wherein the carrier is composed of one or more auxiliaries. Generally, the preparation of the composition comprises: uniformly and directly mixing active ingredients with liquid carriers, diluents, adjuvants and/or excipients or finely isolated solid carriers or both, and, if necessary, shaping the product.

According to the present invention, the compositions suitable for oral administration may be present in the form of separate units each of which contains a predetermined amount of the active ingredient, such as capsules, sachets or tablets; as a powder or granules; as a solution or suspension in an aqueous phase or non-aqueous liquid; or as a oil-in-water liquid emulsion or water-in-oil emulsion. The active ingredient may also be present in the form of a bolus, electuary or paste.

Tablets can be prepared by optionally tableting or molding with one or more auxiliaries. Compressed tablets can be prepared by pressing active ingredients in free-flowing form, such as, powder or granules, in a suitable machine, optionally mixed with binders (e.g., inert diluents, preservatives, disintegrants, sodium starch glycolate, crosslinked polypovidone, crosslinked sodium carboxymethylcellulose), surfactants or dispersing agents. Moulded tablets may be prepared by shaping a mixture of powdered compounds wetted with inert liquid diluents in suitable machines. Optionally, the tablets may be coated or scored, the active ingredients may be formulated to provide slow or controlled release of the active ingredient, for example, hydroxypropylmethylcellulose in various proportions are used to produce desired release properties. Optionally the tablets may have an enteric coating to release active ingredients in the intestine rather than in the stomach.

Compositions suitable for parenteral administration include aqueous and non-aqueous isotonic sterile injection solutions, which may contain antioxidants, buffers, antimicrobial agents and solutes which allow the compositions to be isotonic with the blood of the patient expected; and aqueous and non-aqueous sterile suspensions which may include suspending agents and thickening agents. The compositions may be present in unit-dose or multi-dose sealed containers, such as ampoule and tubes, may be stored in a freeze-dried (lyophilized) condition, only sterile liquid carriers such as water for injection should be added prior to use. Extemporaneous injection solutions and suspensions may be prepared with above kinds of sterile powders, granules and tablets.

Compositions suitable for topical application to the skin, i.e., the compositions by transdermal administration may contain active agents dissolved or suspended in any suitable carriers or matrixes, which may be in the form of lotions, gels, creams, pastes, ointments and the like. Suitable carriers can include liquid paraffin, propylene glycol, waxes, polyoxyethylene, and long chain alcohols. Transcutaneous device such as patch may also be used, which may comprise microporous membranes prepared with suitable materials such as nitrate/cellulose acetate, propylene and polycarbonate. The patches may also contain suitable skin adhesive and substrate materials.

The active compounds according to the invention may also be present in the form of an implant, which may comprise polymerizable devices of drugs, wherein polymers are biocompatible and non-toxic. Suitable polymers may include hydrogels, silicones, polyethylenes and biodegradable polymers.

The compounds of the invention may be administered in sustained release (i.e., controlled release) or slow-release form. The sustained release formulations are formulations in which the active ingredients slowly release in the body of patients after administration and maintain desired concentration of drugs in minimum time. The preparation of sustained release formulations are known to those skilled in the art. Dosage forms may include oral forms, implants and transdermal forms. For sustained release administration, active ingredients may be used as, for example, sustained release particles suspensions in liposomes.

Suitable dosage ranges of the compounds according to the present invention are selected according to the specific activity of the compounds selected, the condition of patients and the conditions to be treated. Those skilled in the art can select suitable dosage ranges according to their general knowledge and experience in the art. For example, as to influenza, a suitable human dosage can range 1-500 mg per person per day, for example, 10-300 mg, usually 30-150 mg.

Evaluation method of biological activity of the compounds of the invention in inhibiting entry of influenza viruses into cells Cytopathic Effect (CPE) Inhibition Assay.

The infection of Influenza virus leads to cytopathic so that the cell viability is decreased. If drugs can inhibit replication of influenza virus, the cytopathic effect will be reduced, and cell viability will be improved. In particular:

1) Canine kidney epithelial cells (MDCK) seeded in 1:3 ratio to white 96-well plates, cultured with 10% FBS-containing DMEM medium in cell incubator at 37° C. for 24 h.

2) The influenza virus [A/WSN/33(H1N1), a multiplicity of infection (MOI)=1] and a concentration of the compound to be tested were added to 100 µl of DMEM containing trypsin treated with 2 µg/mL TPCK and 1% FBS, and mixed well. Negative control compound was 1% DMSO (the solvent used for diluting compounds). Meanwhile, an experimental group was arranged to which only compounds were added without viruses to determine the effect of the compounds on cell viability.

3) The culture medium of MDCK cells in 96-well plates was aspirated, the culture medium mixed with viruses and compounds was added to MDCK cells, cultured in cell incubator at 37° C. 48 h. Three replicates for each sample.

4) The cell viability was detected using CellTiter-Glo fluorescent cell viability assay kit (Cat.G7571, Promega). Cells and CellTiter-Glo reagent were placed in room temperature environment, until the temperature thereof was equilibrated to room temperature. 100 µl/well CellTiter-Glo reagent was added to the culture supernatant of cells, shaked for 2 min, stood in dark for 10 min. The cell viability was detected using Tecan Infinite M2000 PRO™ instruments.

5) Calculation method of $EC_{50}$: the compounds were diluted in concentration series, and then the cell viability was detected using the above method. Protective rate of compound against cell lesion=100×(1−(Test compound−Median Virus1)/(Median Cells−Median Virus2)), wherein Test compound represents the cell viability of the group in which only compound to be tested was added without viruses; Median Virus1 represents the cell viability of the group in which compound to be tested and viruses were added; Median Cells represent the cell viability of the group in which only 1% DMSO was added; Median Virus2 represents the cell viability of the group in which 1% DMSO and viruses were added. The concentration of the compounds and the corresponding protective rate were fed to software Prism, and then $EC_{50}$ was calculated. This method has been widely used in the field of antiviral drug screening (Noah, Severson, et al. 2007).

6) Calculation method of $CC_{50}$: the cytotoxicity of the compound was also detected by CellTiter-Glo. Compounds were diluted in a series of concentrations, and then added to the cells. The method was as described in 2)-4), but without the addition of viruses. After incubation for 48 h, the cell viability was measured. Then the cell viability (1% DMSO) in the control group was defined as 100%, the cell viability of each of other compounds groups was standardized, by being divided by the cell viability of 1% DMSO in control group, and then multiplied by 100%. The concentration of the compound and the corresponding standardized cell viability were input to the software Prism, and thereby $CC_{50}$ was calculated.

2. Plaque Inhibition Assay.

Plaque inhibition experiments was used to further verify the antiviral effect of compounds.

Specific methods were described as follows:

1) MDCK cells were passaged to 12-well plates, cultured with DMEM culture medium containing 10% FBS at 37° C. for 24 h, so that the cell density reached $0.4 \times 10^6$ cells/well. The cells were washed with PBS once.

2) A/WSN/33 (H1N1) virus (100 PFU/well) and serially diluted compounds were mixed. The diluent was DMEM containing 2 µg/mL TPCK-treated trypsin. The mixture was added to MDCK cells, the attachment was allowed at 37° C. for 1 h 3) The virus solution was aspirated, the cells were washed three times with PBS to remove unbound viruses.

4) the cells were covered with 1 mL DMEM containing 1.5% low melting point agarose, compound to be tested, 2 µg/mL TPCK-treated trypsin without phenol red. Please note: the temperature should not be too high to avoid the cells being burnt to death.

5) After agarose was solidified at 4° C. (10-15 min), it was put in upside down in an incubator at 37° C. In 3-4 days, the plaques were counted to calculate the virus titer. If the compound inhibited the virus, the number of the plaque was decreased.

3. Time-of-Addition Experiment:

This experiment was explored to analyze which stage of the influenza virus life cycles was targeted by the compound. The details were:

1) MDCK cells were passaged into six-well plates and cultured in a cell incubator at 37° C. with 10% FBS-containing DMEM medium for 24 h.
2) A/WSN/33(H1N1) virus (MOI=1) was diluted to serum-free DMEM medium, infected MDCK cells.
3) The replication cycle of influenza virus from adsorption to release of progeny virions was about 6-8 h. Therefore, the drug was added to the cell culture medium in the following period of time: 0-10, 0-2, 2-5, 5-8 or 8-10 h.
4) 10 h post-infection, the cell was washed with ice-cold PBS once and lysed with 200 µl/well of PIPA lysate. The cells were scraped with a cell scraper, suctioned into 1.5 mL EP tube and placed on ice for 15 min. The EP tubes were centrifuged at 4° C., 12000 rpm for 10 min, and the supernatant was transferred to another 1.5 mL EP tube.
5) 30 µl of the sample was mixed with equal volume of 2× protein loading buffer, and boiled at 100° C. for 10 min.
6) 20 µl of the boiled sample was added to 12% protein gel loading channel and SDS-PAGE electrophoresis was performed.
7) The expression level of NP protein of influenza virus was detected by immunoblotting (Western blotting) (by which the replication of virus in cell was detected); at the same time, cell protein GAPDH was used as internal control (it can also be used to verify the cytotoxicity of the drug).

4. Pseudotype Virus Experiments.

Pseudotype virus experiments of influenza virus with highly safety and operability were used to verify whether a compound acts on the entry stage of influenza virus life cycle, and whether the compound could inhibit other highly pathogenic influenza strains. Pseudotype influenza viruses are recombinant virus particles, the core of which is derived from retroviral genome (excluding HIV genome packaging genes), and the outer layer comprises the influenza virus envelope protein hemagglutinin (HA) and neuraminidase (NA). This recombinant virus can infect cells as influenza viruses, but can only replicate once and can not package progeny viruses.

Preparation of Pseudotype Virus and Specific Methods of Compounds Inhibiting Pseudotype Virus Infection Experiments 1) HA and NA genes of influenza viruses were cloned into eukaryotic expression vector pcDNA4/TO, and performed to sequencing detection.
2) The plasmids were extracted using plasmid MIDI kit (Promega), the concentration and purity of plasmids were measured by spectrophotometry, for next step transfection.
3) The 293T cells were passaged to 10 cm cell culture dish, cultured at 37° C. for 24 h. The cell medium was changed in 1-2 h before transfection.
4) pcDNA4/TO-HA, pcDNA4/TO-NA and pNL4-3.Luc. E-R-carrier each 6 µg were co-transfected into 293T cells using transfection reagent lipofectamine2000 (Invitrogen). The medium was changed in 4-6 h after the transfection. Specific steps of transfection were as described in lipofectamine2000 (Invitrogen) product specification. The transfected cells were cultured at 37° C. for 72 h.
5) Pseudotype influenza virus particles were secreted into the culture supernatant. The cell culture supernatant containing pseudotype viruses was filtered through 0.45 µM pore-size filters to remove cells and cell debris in the culture medium.
6) The pseudotype viruses were stored at −80° C., VSV pseudotype virus was prepared in the same method as described above, wherein pcDNA4/TO-HA and pcDNA4/TO-NA of influenza viruses were replaced with a plasmid expressing VSVG.
7) MDCK cells were seeded into black clear bottom 96-well plates, and cultured at 37° C. for 24 h.
8) The compound to be tested and the diluted pseudotype virus were mixed thoroughly in DMEM containing 2 µg/mL TPCK treated trypsin and 1% FBS.
9) The cell culture medium in 96 well plates was aspirated, and then the 100 µl/well mixture was added to the cells, cultured at 37° C. for 48 h. Each compound three wells, each compound contained a set of VSV pseudotype virus experimental group to detect the specificity of the compounds to influenza pseudotype viruses.
10) The activity of luciferase in the infected cells was detected by Bright-glo Luciferase Assay System (Promega). Firstly, the cell culture plates and detection reagents were placed in room temperature environment to allow their temperature to be equilibrated to room temperature; and 100 µl/well detection reagent was added to 96-well plates, shocked for 10 s, stood in dark for 2 min; and then the activity of luciferase was measured by spectrophotometer.

Genes necessary for viral replication were deficient in the pseudotype virus genome prepared, so the pseudotype virus lost replication capability, with high safety. In addition to A/WSN/33 (H1N1) strain, the influenza virus strain to be selected included A/VietNam/1203/2004 (H5N1), because this strain was highly pathogenic influenza virus strain. HA and NA genes of these strains can be purchased from Beijing Sino Biological Technology Co., Ltd., without operation of live viruses. Therefore, the experiment was safe. The pseudotype virus particles contained Luciferase reporter gene. Once entering cells, it can express Luciferase gene. After cells were lysed, an enzyme substrate was added. Reading on enzyme-labelled meter.

5. Hemagglutination Inhibition (HI) Assay.

This method is used to detect whether drugs affect the binding of viruses to cellular receptors. Specific methods were as follows:

1) Preparation of 1% (v/v) chicken red blood cell suspension.

1-2 Healthy chickens were chosen. Their blood was collected to the same amount of anticoagulant solution and mixed homogeneously, stored in a refrigerator at 4° C. The mixture was centrifuged at 800-1000 rpm for 5 minutes. The supernatant and the thin layer of white blood cells in the upper layer of red blood cells were discarded using a pipette. The precipitated red blood cells was gently mixed uniformly with physiological saline, and centrifugated in a centrifuged at 800 rpm for 5 minutes, the supernatant was removed, and mixed uniformly with physiological saline, centrifugated. This step was repeated for 4-5 times. After last centrifugation of the red blood cells, the supernatant was removed. The red blood cells could be stored in a refrigerator at 4° C. for 2-3 days. Upon use, 0.1 mL red blood cells was sucked up by a 1 mL pipette, added into 9.9 mL physiological saline, namely 1% erythrocyte suspension.

2) Determination of hemagglutination titer of virus.

WSN influenza virus was diluted in 2-fold serial dilutions, the diluent was PBS.

3) The virus medium and 1% erythrocyte suspension were mixed in equal volume (each 50 µl), added to V bottomed 96-well plates, shaked on micro oscillator for 1 min, and incubated at room temperature for 30 min.

4) When the reaction plate was tilted at 45°, the red blood cells precipitated at the bottom of the well would flow downward in linear state along incline plane, indicating that red blood cells were not or were not completely agglutinated by viruses; if the red blood cells at the well bottom paved the well bottom, agglutinated to uniform thin layer, indicating that the red blood cells were agglutinated by viruses. After the hemagglutination titer of influenza viruses was determined, suitable amount of viruses used was determined.

5) The drug, DMSO (negative control) or anti-HA-specific monoclonal antibody (positive control) were separately mixed with the virus medium and added to cell suspension. The inhibitory effect of compound on hemagglutination was observed.

The present invention was described in detail using the embodiments given below. The embodiments are used only as illustration, and therefore shall not be construed as limitation to the scope of the present invention.

Extraction and Separation of Oleanolic Acid and Echinocystic Acid

Oleanolic acid and echinocystic acid are triterpenoids natural products widely present in plants. They are separated from plants by following methods: plants rich in oleanolic acid and echinocystic acid, such as acacia, etc. were immersed in ethanol with reflux, the portion of large polarity was extracted and treated with concentrated hydrochloric acid to remove sugars contained therein. The purification was performed on silica gel column chromatography, with gradient elution with methylene chloride/methanol, to isolate large quantity of pure oleanolic acid and echinocystic acid ("Extraction and Separation of Natural Organic Compounds" in 1994, Science and Technology Press). Oleanolic acid and echinocystic acid can also be commercially available.

EXAMPLES

Example 1

Synthesis of 3β,16α-dihydroxy-olean-12-en-28-oic acid-28-O-(2,3,4,6-tetra-O-acetyl-β-D-glucoside) and 3β,16α-dihydroxy-olean-12-en-28-oic acid-28-O-(β-D-glucoside)

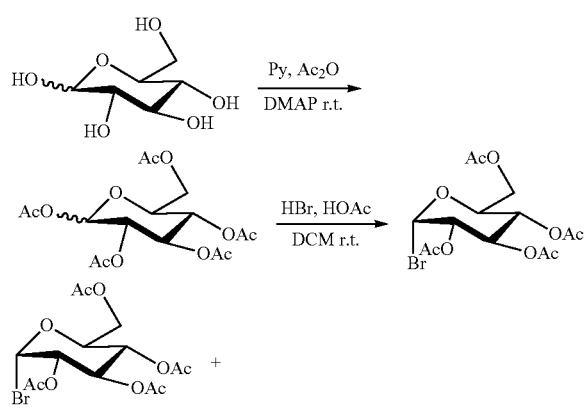

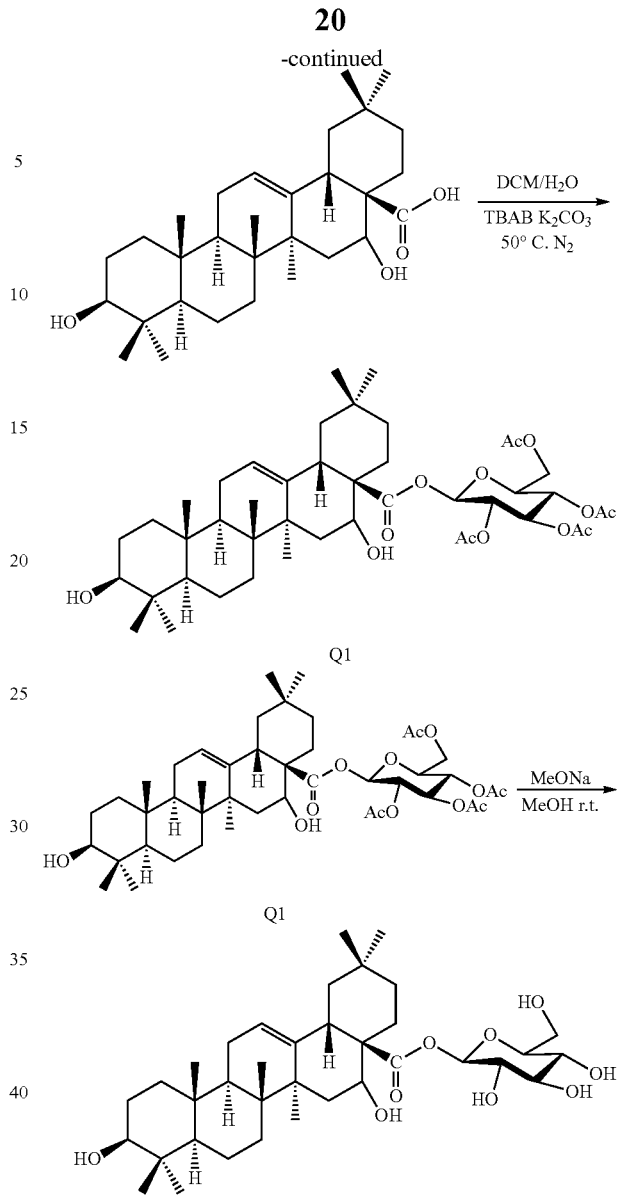

3 g of D-glucose was added in a 50 mL reaction flask, dissolved in 24 mL of pyridine, added successively with 12 mL of acetic anhydride and a catalytic amount of DMAP. The reaction was allowed at room temperature overnight, and then stopped. The reaction was monitored by TLC until the reaction was complete. Eluent PE:AcOEt=1:1. After the solvent was removed by rotary evaporation, the resultant was dissolved with 20 mL eluent (PE:AcOEt=1:1), separated on flash column, standby.

390 mg of the above product was added in a 25 mL reaction flask, dissolved with 3 mL of DCM, slowly added dropwise with 0.21 mL of HBr-AcOH solution in ice bath, The reaction was stirred for 1 h in ice bath and then at room temperature. The reaction was monitored by TLC until the reaction was complete. Eluent PE:AcOEt=2:1. After the reaction was stirred for 12 h, then stopped. The resultant was diluted with 20 mL of DCM, washed successively with 20 mL of distilled water, 20 mL saturated NaHCO₃ solution. The organic layers were combined, dried over MgSO₄, purified on chromatography column under elution condition PE:EA=1:1 to give 194 mg of a yellow viscous substance.

To a 50 mL reaction flask containing 20 mL of bromo sugar (194 mg, 0.47 mmol) in DCM were added 189 mg (0.4 mmol) EA, 138 mg $K_2CO_3$, 52 mg of tetra-n-butylammonium bromide, 2 mL of water. The reaction was stirred at 50° C. with reflux in $N_2$ atmosphere. The reaction was stopped after 12 h. Monitored by TLC, eluent PE:AcOEt=1:1. The resultant was purified on chromatography column under elution conditions PE:AcOEt=2:1 to give 252 mg of white solid compound 3β,16α-dihydroxy-olean-12-en-28-oic acid-28-O (2,3,4,6-tetra-O-acetyl-β-D-glucoside), yield 80%. $^1$H NMR (400 MHz, $CDCl_3$): δ 5.54 (d, 1H, J=8.2 Hz, Glc-1-H), 5.39 (t, 1H, J=3.2 Hz, $H_{12}$), 5.08-5.24 (m, 3H), 4.39 (br t, 1H, $H_{16}$), 4.25 (dd, 1H, J=4.4, 12.4 Hz), 4.02 (dd, 1H, J=2.1, 12.4 Hz), 3.74-3.78 (m, 1H), 3.19 (dd, 1H, J=4.2, 10.6 Hz, $H_3$), 2.97 (dd, 1H, J=4.0, 14.3 Hz, $H_{18}$), 2.05, 2.00, 2.00, 1.99 (s, each 3H, $CH_3CO$), 1.32, 0.96, 0.92, 0.89, 0.88, 0.75, 0.70 (s, each 3H, $H_{27}$, $H_{23}$, $H_{30}$, $H_{25}$, $H_{29}$, $H_{26}$, $H_{24}$). $^{13}$C NMR (100 MHz, $CDCl_3$): δ 174.72 (C=O, $C_{28}$), 170.53, 170.03, 169.38, 169.07, 141.88 ($C_{13}$), 123.22 ($C_{12}$), 91.56 (Glc-1-C), 78.84, 74.22, 72.68, 72.41, 69.91, 67.90, 61.44, 55.19, 48.79, 46.61, 46.03, 41.31, 40.40, 39.49, 38.68, 38.48, 36.93, 35.46, 35.14, 33.02, 32.62, 30.23, 30.17, 28.01, 27.12, 26.76, 24.45, 23.24, 20.62 ($\underline{C}H_3CO$), 20.50 (3C, 3×$\underline{C}H_3CO$), 18.22, 17.01, 15.55, 15.43. ESI-HRMS (m/z) calcd for $C_{44}H_{66}O_{13}Na$ (M+Na$^+$): 825.4396. Found 825.4387; $C_{44}H_{70}O_{13}N$ (M+$NH_4^+$): 820.4842. Found 820.48400. The compound was represented by the following Q1.

50 mg of the compound was dissolved with 5 mL methanol in 25 mL reaction flask, added with an appropriate amount of MeONa, allowed to react at room temperature for 1 h with stirring. The reaction was monitored by TLC until the reaction was complete. Eluent DCM:MeOH=7:1. Upon the completion of the reaction, a cation exchange resin was added, and the pH was adjusted to neutral. The resultant was purified on chromatography column under eluent DCM:MeOH=5:1 to give 12.4 mg of a white solid 3β,16α-dihydroxy-olean-12-en-28-oic acid-28-O-(β-D-glucoside), yield 31%.

1H NMR (400 MHz, MeOD): δ 5.35 (d, 1H, J=8.1 Hz, Glc-1-H), 5.32 (t, 1H, J=3.4 Hz, H12), 4.53 (br t, 1H, H16), 3.82 (d, 1H, J=11.1 Hz), 3.67 (dd, 1H, J=4.3, 12.0 Hz), 3.27-3.34 (m, 4H), 3.15 (dd, 1H, J=5.0, 11.4 Hz), 2.99 (dd, 1H, J=4.0, 14.2 Hz), 2.29 (t, 1H, J=13.3 Hz), 1.37, 0.97, 0.96, 0.89, 0.79, 0.77 (s, 7×CH3). $^{13}$C NMR (100 MHz, MeOD): δ 177.21 (C=O, $C_{28}$), 144.63 ($C_{13}$), 123.63 ($C_{12}$), 95.72 (Glc-1-C), 79.72, 78.73, 78.33, 74.93, 74.01, 71.08, 62.42, 56.88, 50.03, 48.20, 47.78, 42.65, 42.12, 40.82, 39.97, 39.84, 38.16, 36.44, 36.27, 31.70, 31.28, 28.74, 27.27, 25.01, 24.49, 19.50, 17.78, 16.33, 16.10. ESI-HRMS (m/z) calcd for $C_{36}H_{58}O_9Na$ (M+Na$^+$): 657.3973.

Example 2

Synthesis of 3β,16α-dihydroxy-olean-12-en-28-oic acid-28-O-(2,3,4,6-tetra-O-acetyl-β-D-galactopyranoside) and 3β,16α-dihydroxy-olean-12-en-28-oic acid-28-O-(β-D-galactoside)

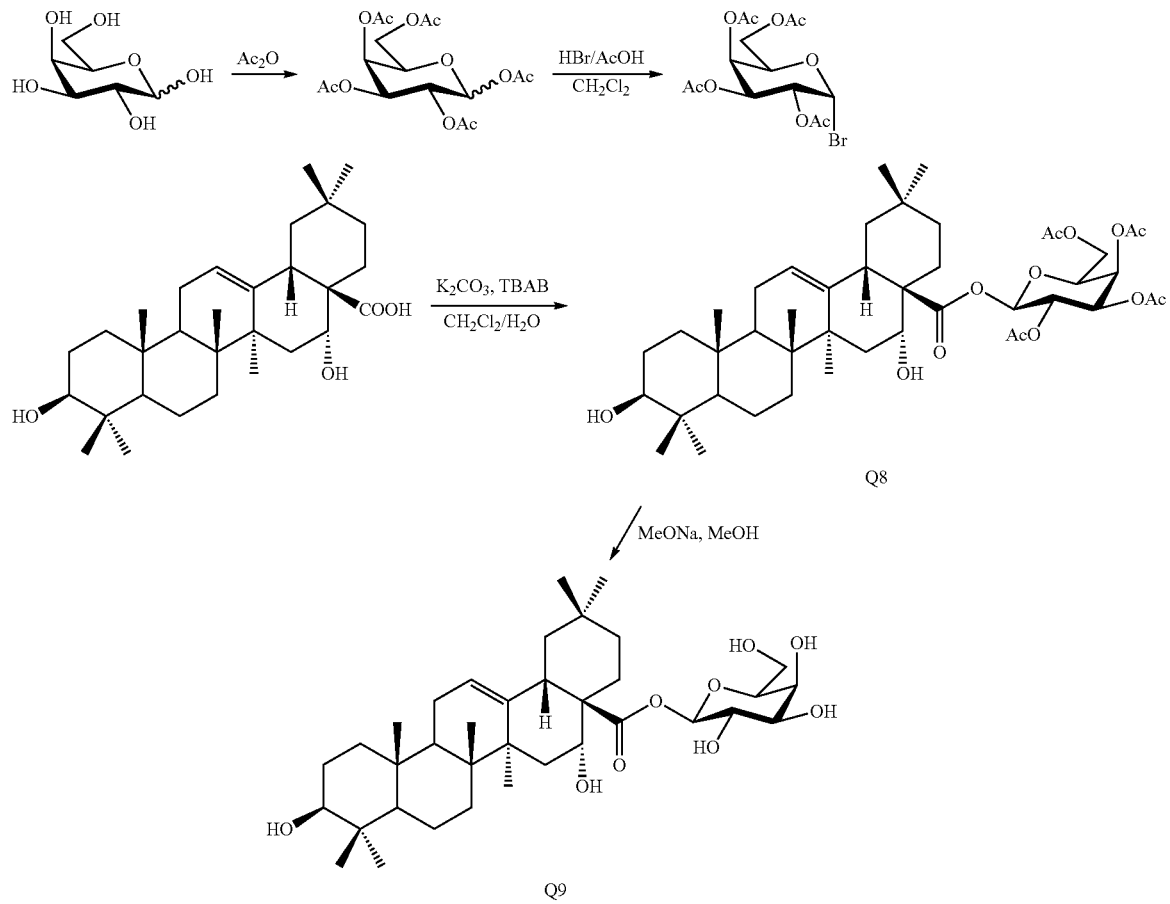

2 g of D-galactose was placed in a 50 mL reaction flask, dissolved in 16 mL of pyridine, added successively with 8 mL of acetic anhydride and a catalytic amount of DMAP, allowed to react at room temperature for 10 h. The reaction was stopped. The completion of the reaction was monitored by TLC. Eluent PE:AcOEt=1:1. After the solvent was removed by rotary evaporation, the resultant was dissolved with 20 mL of DCM, washed with 20 mL of water. The organic layer was dried over $MgSO_4$. The solvent was removed by rotary evaporation to give a solid product of peracetylated galactose.

390 mg of the above product was placed in a 25 mL reaction flask, dissolved with 3 mL of DCM, added dropwise slowly with 0.35 mL of HBr-AcOH solution in ice-bath, allowed to react for 1 h and then to react at room temperature. The reaction was stopped after 12 h. The reaction was monitored by TLC until the reaction was complete. Eluent PE:AcOEt=2:1. The resultant was diluted with 20 mL of DCM, washed successively with 20 mL of distilled water, 20 mL of saturated $NaHCO_3$ solution. The organic layers were combined. The solvent was removed by rotary evaporation to 20 mL.

To a 50 mL reaction flask containing 20 mL of bromo sugar (the unseparated mixture in the above step reaction) DCM solution were added 188.8 mg (0.4 mmol) of EA, 138 mg of $K_2CO_3$, 51.52 mg of tetra-n-butylammonium bromide, and 2 mL of water, allowed to react at 50° C. in $N_2$ atmosphere with reflux. The reaction was stopped after 12 h. The reaction was monitored by TLC until the reaction was complete. Eluent PE:AcOEt=1:1. The resultant was purified on chromatography column under elution condition PE:AcOEt=1:1 to give 98.5 mg of a white solid 3β,16α-dihydroxy-olean-12-en-28-oic acid-28-O-(2,3,4,6-tetra-O-acetyl-β-D-galactopyranoside), yield 31%.

$^1$H NMR (400 MHz, $CDCl_3$): δ 5.54 (d, 1H, J=8.4 Hz, Gal-1-H), 5.40-5.44 (m, 2H), 5.31 (t, 1H, J=10.3 Hz), 5.07 (dd, 1H, J=3.4, 10.4 Hz), 4.39 (br t, 1H, H16), 4.10-4.15 (m, 2H), 4.00 (t, 1H, J=6.7 Hz), 3.22 (dd, 1H, J=4.1, 10.4 Hz, $H_3$), 3.00 (d, 1H, J=10.6 Hz, His), 2.17, 2.04, 2.02, 1.99 (s, each 3H, $CH_3CO$), 1.34, 0.99, 0.95, 0.92, 0.91, 0.78, 0.75 (s, each 3H, $CH_3$, $H_{27}$, $H_{23}$, $H_{30}$, $H_{25}$, $H_{29}$, $H_{26}$, $H_{24}$). $^{13}$C NMR (100 MHz, $CDCl_3$): δ 174.64 (C=O, $C_{28}$), 170.22, 170.07, 169.84, 169.25, 141.87 ($C_{13}$), 123.13 ($C_{12}$), 92.03 (Gal-1-C), 78.82, 74.06, 71.39, 70.70, 67.56, 66.69, 60.65, 55.22, 48.97, 46.64, 46.07, 41.36, 40.48, 39.53, 38.69, 38.49, 36.95, 35.50, 35.06, 33.04, 32.58, 30.19, 29.82, 28.01, 27.13, 26.76, 24.65, 23.26, 20.64, 20.55, 20.44, 18.22, 17.07, 15.55, 15.47. ESI-HRMS (m/z) calcd for $C_{44}H_{66}O_{13}Na$ (M+$Na^+$): 825.4396. Found 825.4387; $C_{44}H_{70}O_{13}N$ (M+$NH_4^+$): 820.4842. Found 820.4839.

50 mg of the above compound was dissolved with 5 mL of methanol in 25 mL reaction flask, added with an appropriate amount of MeONa, allowed to react at room temperature for 1 h. Monitored by TLC, eluent DCM:MeOH=7:1. A cation exchange resin was added. The pH was adjusted to neutral. Filtered, the filtrate was removed by rotary evaporation. The resultant was purified on chromatography column under eluent DCM:MeOH=5:1 to give 35.6 mg of a white solid 3β,16α-dihydroxy-olean-12-en-28-oic acid-28-O-(β-D-galactoside), yield 90%.

$^1$H NMR (400 MHz, MeOD): δ 5.31-5.33 (m, 2H, Gal-1-H, $H_{12}$), 4.55 (br t, 1H, $H_{16}$), 3.88 (d, 1H, J=3.0 Hz), 3.69-3.71 (m, 2H), 3.58-3.65 (m, 2H), 3.50 (dd, 1H, J=3.2, 9.7 Hz), 3.15 (dd, 1H, J=4.9, 11.4 Hz, $H_3$), 3.00 (dd, 1H, J=3.8, 14.2 Hz, $H_{18}$), 2.29 (t, 1H, J=13.3 Hz), 1.37, 0.97, 0.96, 0.89, 0.78, 0.77 (s, 7×$CH_3$). $^{13}$C NMR (100 MHz, MeOD): δ 177.29 (C=O, $C_{28}$), 144.64 ($C_{13}$), 123.63 ($C_{12}$), 96.22 (Gal-1-C), 79.72, 77.38, 75.17, 74.94, 71.30, 70.00, 62.02, 56.88, 49.98, 42.63, 42.08, 40.81, 39.96, 39.83, 38.16, 36.44, 36.26, 34.23, 33.36, 31.80, 31.29, 28.74, 27.90, 27.28, 24.99, 24.48, 19.50, 17.79, 16.33, 16.09. ESI-HRMS (m/z) calcd for $C_{36}H_{62}O_9N$ (M+$NH_4^+$): 652.4419. Found 652.4415.

Other derivatives were synthesized by methods similar to the methods described above in the examples, for examples, following compounds

| Compound No. | Formula |
|---|---|
| Q1 | |
| Q2 | |
| Q3 | |
| Q4 | |
| Q5 | |

| Compound No. | Formula |
|---|---|
| Q6 | 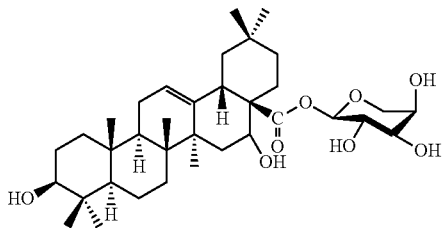 |
| Q8 | 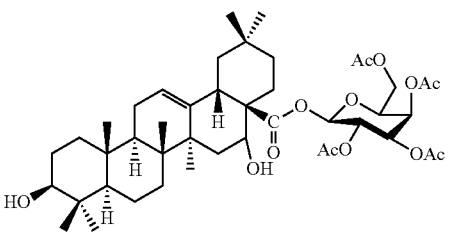 |
| Q9 | 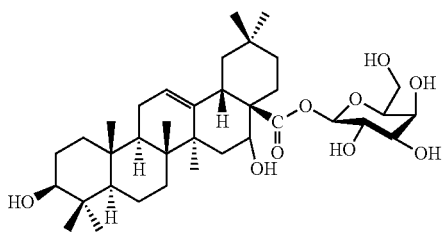 |
| Q10 | 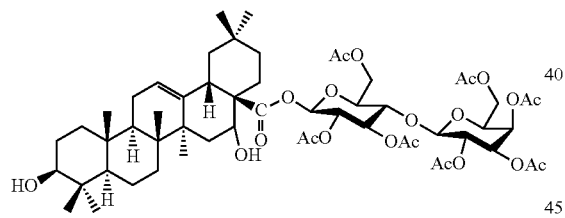 |
| Q11 | 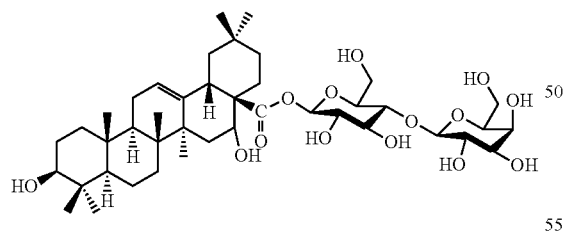 |
| Q12 | 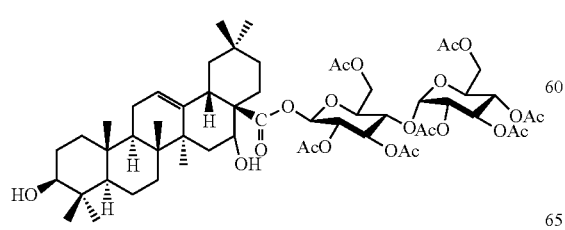 |

| Compound No. | Formula |
|---|---|
| Q13 | 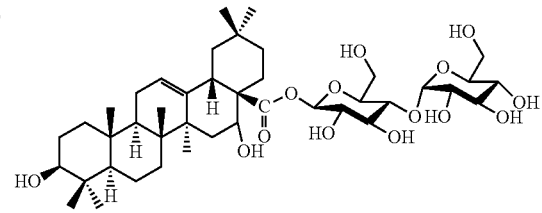 |
| Q14 | 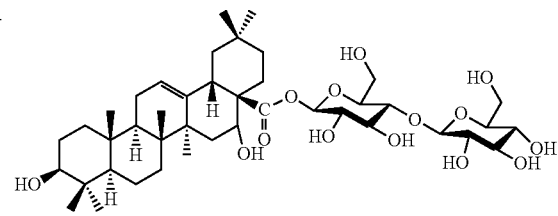 |

Q1: 3β,16α-dihydroxy-olean-12-en-28-oic acid-28-O-(2,3,4,6-tetra-O-acetyl-β-D-glucoside)
Q2: 3β,16α-dihydroxy-olean-12-en-28-oic acid-28-O-(β-D-glucoside)
Q3: 3β,16α-dihydroxy-olean-12-en-28-oic acid-28-O-(2,3,4-tri-O-acetyl-β-D-xyloside)
Q4: 3β,16α-dihydroxy-olean-12-en-28-oic acid-28-O-(β-D-xyloside)
Q5: 3β,16α-dihydroxy-olean-12-en-28-oic acid-28-O-(2,3,4-tri-O-acetyl-β-D-arabinoside)
Q6: 3β,16α-dihydroxy-olean-12-en-28-oic acid-28-O-(β-D-arabinoside)
Q8: 3β,16α-dihydroxy-olean-12-en-28-oic acid-28-O-(2,3,4,6-tetra-O-acetyl-α-D-galactoside)
Q9: 3β,16α-dihydroxy-olean-12-en-28-oic acid-28-O-(β-D-galactoside)
Q10: 3β,16α-dihydroxy-olean-12-en-28-oic acid-28-O-(hepta-O-acetyl-β-D-lactoside)
Q11: 3β,16α-dihydroxy-olean-12-en-28-oic acid-28-O-(β-D-lactoside)
Q12: 3β,16α-dihydroxy-olean-12-en-28-oic acid-28-O-(hepta-O-acetyl-β-D-maltoside)
Q13: 3β,16α-dihydroxy-olean-12-en-28-oic acid-28-O-(β-D-maltoside)
Q14: 3β,16α-dihydroxy-olean-12-en-28-oic acid-28-O-(β-D-cellobioside)

Example 3

Synthesis of 3β-hydroxy-olean-12-en-28-oic acid-28-N-(2,3,4,6-tetra-O-acetyl-β-D-galactoside) and 3β-hydroxy-olean-12-en-28-oic acid-28-N-(β-D-galactoside)

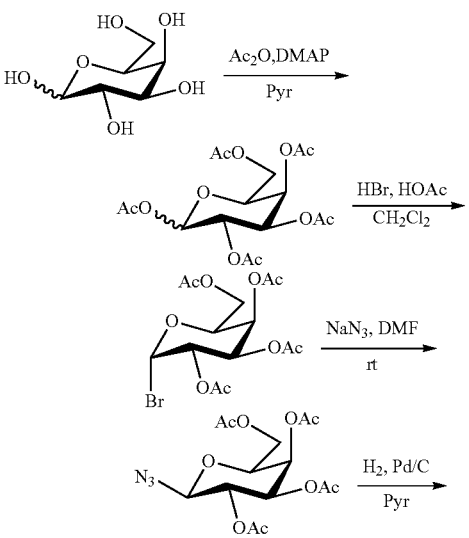

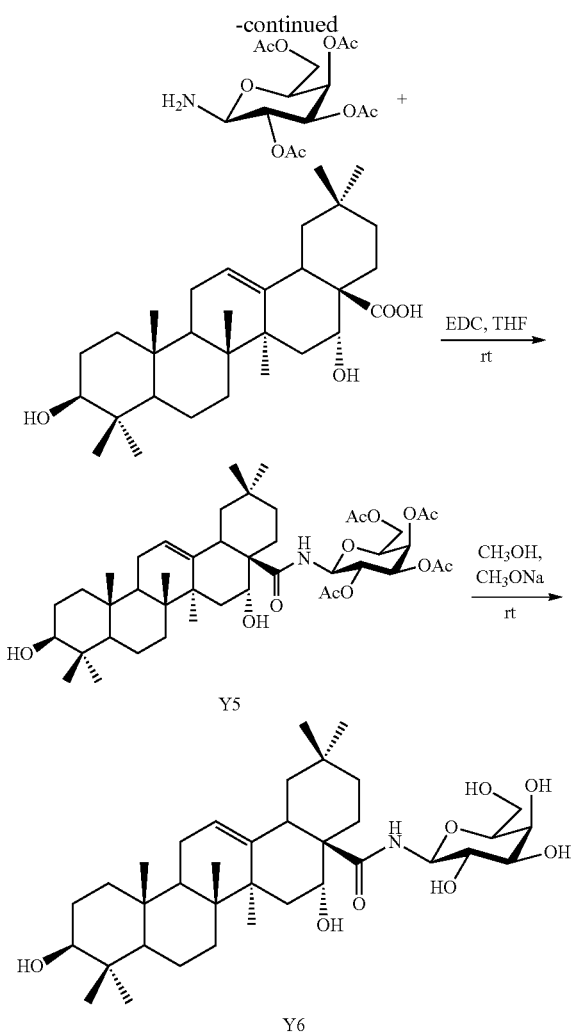

Preparation of 1,2,3,4,6-penta-O-acetyl-β-D-galactose 3 g of D-galactose was placed in a 50 mL reaction flask, dissolved in 24 mL of pyridine, added successively with 12 mL of acetic anhydride and a catalytic amount of DMAP. The reaction was stirred at room temperature overnight. Then the reaction monitored by TLC until the reaction was complete. The solvent was removed by rotary evaporation. The resultant was mixed with 50 mL AcOEt to give a suspension, washed successively with 50 mL of distilled water three times and with 50 mL of saturated brine. The organic layer was dried over anhydrous $Na_2SO_4$ and purified on silica gel column to give the product.

Preparation of 1α-bromo-2,3,4,6-tetra-O-acetyl-β-D-galactose 2.0 g of the above product was placed in a 25 mL reaction flask, dissolved with 15 mL of DCM, added dropwise slowly with 1.2 mL of HBr-AcOH solution in ice bath, allowed to react for 1 h and then to react at room temperature overnight. The reaction was monitored by TLC until the reaction was complete. Eluent PE:AcOEt=2:1. The resultant was diluted with 20 mL of DCM, washed successively with 40 mL of distilled water three times and 40 mL of saturated $NaHCO_3$ solution. The organic phase was dried over $Na_2SO_4$. The solvent was removed by rotary evaporation. The resultant was directly performed to next step of the reaction without further separation and purification.

Preparation of 1β-azido-2,3,4,6-tetra-O-acetyl-β-D-galactose

The above product was dissolved with 10 mL of DMF, added with $NaN_3$ with stirring, allowed to react at room temperature overnight. The reaction was monitored by TLC until the reaction was complete. Eluent PE:AcOEt=2:1. The solvent was removed by rotary evaporation. The resultant was mixed with 50 mL of AcOEt to give a suspension, washed successively with 50 mL of distilled water three times and with 50 mL of saturated brine. The organic layer was dried over anhydrous $Na_2SO_4$ and purified on silica gel column to give about 0.97 g of a white solid, 50% total yield in the two steps.

100 mg of the above product was dissolved with 5 mL of THF, catalytically hydrogenated in the presence of Pd/C catalyst, allowed to react at room temperature overnight. The reaction was monitored by TLC until the reaction was complete. Eluent PE:AcOEt=1:1. After Pd/C was filtered off, the filtrate was removed by rotary evaporation. The product was directly performed to next step of the reaction without further purification treatment.

Preparation of 3β,16α-dihydroxy-olean-12-en-28-oic acid-28-N-(2,3,4,6-tetra-O-acetyl-β-D-galactoside)

150 mg of EA was dissolved with 5 mL THF, added with 65 mg of EDC, allowed to react at room temperature for 0.5 h with stirring, added with the above product, allowed to react at room temperature for 1 d. The reaction was monitored by TLC until the reaction was complete. Eluent PE:AcOEt=1:1. The solvent was removed by rotary evaporation. The resultant was mixed with 30 mL AcOEt to give a suspension, washed successively with 30 mL of distilled water three times and with 30 mL of saturated brine. The organic layer was dried over anhydrous $Na_2SO_4$, and purified on silica gel column to give about 114.3 mg of a white solid, 53% total yield in the two steps.

$^1$H NMR (400 MHz, $CDCl_3$): δ 0.79, 0.80, 0.90, 0.91, 0.92, 0.99, 1.16, 2.00, 2.02, 2.05, 2.14 (11×$CH_3$), 0.72-2.17 (m, other aliphatic ring protons), 2.55 (brd, 1H, J=9.9 Hz), 3.21 (dd, 1H, J=3.6, 10.4 Hz), 3.97-4.13 (m, 3H), 5.03-5.18 (m, 3H), 5.41-5.43 (m, 1H), 5.50 (brs, 1H), 6.68 (d, 1H, J=9.0 Hz). $^{13}$C NMR (100 MHz, $CDCl_3$): δ 15.3, 15.5, 17.0, 18.2, 20.4, 20.5, 20.5, 20.7, 23.1, 23.4, 23.9, 25.4, 27.0, 27.1, 28.0, 30.5, 32.4 (2C), 32.8, 34.0, 36.8, 38.4, 38.6, 39.2, 41.2, 41.9, 46.3, 46.5, 47.4, 55.0, 60.6, 67.0, 68.2, 70.7, 71.6, 78.5, 78.7, 123.4, 143.6, 169.7, 169.9, 170.2, 171.0, 178.9.

Preparation of 3β,16α-dihydroxy-olean-12-en-28-oic acid-28-N-(β-D-galactoside)

50 mg of the above product was dissolved in 3 mL $CH_3OH$, added with an appropriate amount of $CH_3ONa$ with stirring, allowed to react at room temperature for 1 h with stirring. The reaction was monitored by TLC until the reaction was complete. Eluent DCM:MeOH=7:1. Upon the completion of the reaction, a cation exchange resin was added. The pH was adjusted to neutral. The resultant was purified on chromatography column under eluent DCM:MeOH=10:1 to give 35.1 mg of a white solid, 89% yield.

¹H NMR (400 MHz, MeOD): δ0.75, 0.80, 0.90, 0.91, 0.92, 0.96, 1.15 (s, 7×CH₃), 0.71-2.10 (m, other aliphatic ring protons), 2.83 (brd, 1H, J=12.9 Hz), 3.14 (dd, 1H, J=5.0, 11.3 Hz), 3.48-3.55 (m, 3H), 3.62-3.71 (m, 2H), 3.89 (brd, 1H), 4.80 (d, 1H, 8.0 Hz), 5.31 (brs, 1H). ¹³C NMR (100 MHz, MeOD): δ 15.8, 16.1, 17.7, 19.2, 23.9 (2C), 24.0, 24.3, 26.3, 27.5, 28.1, 28.6, 31.3, 33.4, 33.6 (2C), 34.9, 37.8, 39.5, 40.3, 42.0, 42.7, 47.3, 47.3, 48.7, 56.3, 62.2, 70.0, 71.0, 75.4, 77.7, 79.4, 81.5, 123.6, 144.9, 181.1.

Other derivatives were synthesized by methods similar to the methods described in the above examples, for examples, following compounds:

| Compound No. | Formula |
|---|---|
| Y1 | |
| Y2 | |
| Y3 | |
| Y4 | |
| Y5 | |
| Y6 | |
| Y7 | |
| Y8 | |
| Y9 | |
| Y10 | |
| Y11 | |

-continued

| Compound No. | Formula |
|---|---|
| Y12 | |
| Y13 | |
| Y14 | |
| Y15 | |
| Y16 | |

The NMR data of other compounds obtained were as follows:

Y1: 3β,16α-dihydroxy-olean-12-en-28-oic acid-28-N-(2,3,4,6-tetra-O-acetyl-β-D-galactoside)

$^1$H NMR (400 MHz, CDCl$_3$): δ 0.74, 0.79, 0.84, 0.91, 0.93, 1.00, 1.34, 1.99, 2.02, 2.03, 2.13 (s, 11×CH3), 0.74-2.37 (m, other aliphatic ring protons), 2.97 (brd, 1H, J=10.7 Hz), 3.19 (dd, 1H, J=4.2, 10.6 Hz), 3.74-3.78 (m, 1H), 4.02 (dd, 1H, J=2.1, 12.4 Hz), 4.25 (dd, 1H, J=4.4, 12.4 Hz), 4.39 (brs, 1H), 5.08-5.24 (m, 3H), 5.39 (t, 1H, J=3.2 Hz, H12), 5.54 (d, 1H, J=8.2 Hz). $^{13}$C NMR (100 MHz, CDCl$_3$): δ 15.4, 15.6, 17.0, 18.2, 20.5 (3C), 20.6, 23.2, 24.5, 26.8, 27.1, 28.0, 30.2, 30.2, 32.6, 33.0, 35.1, 35.5, 36.9, 38.5, 38.7, 39.5, 40.4, 41.3, 46.0, 46.6, 48.8, 55.2, 61.4, 67.9, 69.9, 72.4, 72.7, 74.2, 78.8, 91.6, 123.2, 141.9, 169.1, 169.4, 170.0, 170.5, 174.7.

Y2: 3β,16α-dihydroxy-olean-12-en-28-oic acid-28-N-(β-D-galactoside)

$^1$H NMR (400 MHz, MeOD): δ 0.78, 0.86, 0.90, 0.95, 0.96, 0.98, 1.33 (s, 7×CH$_3$), 0.74-1.94 (m, other aliphatic ring protons), 2.20 (t, 1H, J=13.4 Hz), 3.04 (dd, 1H, J=3.6, 14.0 Hz), 3.15 (dd, 1H, J=4.9, 11.2 Hz), 3.49-3.56 (m, 3H), 3.65-3.67 (m, 2H), 3.88 (brd, 1H, J=1.4 Hz), 4.26 (dd, 1H, J=3.6, 5.5 Hz), 4.79 (d, 1H, J=8.8 Hz), 5.45 (brs, 1H). $^{13}$C NMR (100 MHz, MeOD): δ16.3, 16.3, 18.2, 19.5, 24.5, 26.3, 27.5, 27.9, 28.7, 29.6, 30.9, 33.1, 34.0, 35.8, 36.3, 38.1, 39.8, 40.0, 41.0, 42.2, 43.0, 47.8, 48.4, 50.8, 56.9, 62.4, 70.4, 71.6, 75.0, 75.8, 78.1, 79.7, 81.9, 123.9, 144.6, 181.1.

Y3: 3,16-dione-olean-12-en-28-oic acid-28-N-(2,3,4,6-tetra-O-acetyl-(β-D-galactoside)

$^1$H NMR (400 MHz, CDCl$_3$): δ 0.82, 0.90, 0.93, 1.05, 1.06, 1.09, 1.22, 2.00, 2.03, 2.04, 2.16 (11×CH$_3$), 1.25-2.65 (m, other aliphatic ring protons), 3.22 (dd, 1H, J=3.8, 13.7 Hz), 3.97-4.00 (m, 1H), 4.06-4.08 (m, 2H), 5.09-5.10 (m, 3H), 5.42 (brs, 1H), 5.68 (brt, 1H), 6.76 (d, 1H, J=7.8 Hz). $^{13}$C NMR (100 MHz, CDCl$_3$): δ 14.9, 17.0, 19.3, 20.4, 20.5 (2C), 20.7, 21.3, 23.0, 23.4, 26.3, 27.1, 28.6, 30.3, 31.9, 32.6, 33.9, 34.9, 36.6, 38.9, 39.6, 44.4, 45.6, 45.9, 46.0, 46.5, 47.3, 55.2, 59.9, 60.7, 67.0, 67.9, 70.7, 71.9, 78.7, 124.5, 140.1, 169.6, 169.9, 170.2, 170.7, 172.3, 210.3, 216.9.

Y4: 3,16-dione-olean-12-en-28-oic acid-28-N-(β-D-galactoside)

$^1$H NMR (400 MHz, MeOD): δ 0.87, 0.95, 0.97, 1.05, 1.08, 1.09, 1.20 (s, 7×CH$_3$), 1.15-2.27 (m, other aliphatic ring protons), 2.36-2.42 (m, 1H), 2.54-2.63 (m, 1H), 2.98 (d, 1H, J=14.7 Hz), 3.43 (dd, 1H, J=3.9, 14.1 Hz), 3.47-3.58 (m, 3H), 3.66-3.67 (d, 2H, J=6.2 Hz), 3.89 (brd, 1H, J=2.7 Hz), 4.82 (d, 1H, J=8.8 Hz), 5.56 (t, 1H, J=3.5 Hz). $^{13}$C NMR (100 MHz, MeOD): δ15.5, 17.8, 20.6, 21.9, 23.7, 24.6, 27.0, 27.7, 28.6, 31.4, 33.2, 33.3, 35.0, 36.1, 37.9, 40.1, 41.1, 46.7 (2C), 47.1, 48.0, 48.5, 48.9, 56.4, 61.1, 62.2, 70.3, 71.1, 75.9, 78.2, 81.8, 125.2, 142.0, 175.1, 212.7, 220.2

Y7: 3β-hydroxy-olean-12-en-28-oic acid-28-N-(2,3,4,6-tetra-O-acetyl-β-D-mannoside)

$^1$H NMR (400 MHz, CDCl$_3$): δ 0.78, 0.79, 0.87, 0.90, 0.92, 0.99, 1.16, 1.98, 2.04, 2.07, 2.23 (11×CH$_3$), 0.71-2.13 (m, other aliphatic ring protons), 2.45 (dd, 1H, J=3.7, 13.2 Hz), 3.21 (dd, 1H, J=4.1, 10.4 Hz), 3.71-3.75 (m, 1H), 4.05 (dd, 1H, J=2.4, 12.2 Hz), 4.22 (dd, 1H, J=4.9, 12.3 Hz), 5.10 (dd, 1H, J=3.3, 10.1 Hz), 5.19-5.24 (m, 1H), 5.31-5.34 (m, 2H), 5.51 (d, 1H, J=9.3 Hz), 6.54 (d, 1H, J=9.3 Hz). $^{13}$C NMR (100 MHz, CDCl3): δ 15.3, 15.5, 16.9, 18.2, 20.4, 20.6 (3C), 23.2, 23.5, 24.0, 25.4, 27.0 (2C), 28.0, 30.5, 32.3, 32.3, 32.8, 33.9, 36.8, 38.4, 38.6, 39.2, 41.9, 42.1, 46.5, 46.6, 47.4, 55.0, 62.4, 65.5, 70.1, 71.4, 73.6, 76.0, 78.7, 122.8, 144.6, 169.7, 169.7, 169.9, 170.5, 178.0.

Y8: 3β-hydroxy-olean-12-en-28-oic acid-28-N-(β-D-galactoside)

$^1$H NMR (400 MHz, MeOD): δ 0.78, 0.85, 0.92, 0.94, 0.95, 0.98, 1.19 (s, 7×CH$_3$), 0.74-2.17 (m, other aliphatic ring protons), 2.83 (dd, 1H, J=3.6, 13.4 Hz), 3.15 (dd, 1H, J=5.0, 11.4 Hz), 3.25-3.28 (m, 1H), 3.50-3.57 (m, 2H), 3.64 (dd, 1H, J=5.6, 11.7 Hz), 3.74 (brd, 1H, J=1.4 Hz), 3.81 (dd, 1H, J=2.2, 11.7 Hz), 5.11-5.13 (m, 1H), 5.39 (brs, 1H), 7.40 (d, 1H, J=8.8 Hz). $^{13}$C NMR (100 MHz, MeOD): δ16.0, 16.3, 18.1, 19.5, 23.9, 24.6 (2C), 26.3, 27.9, 28.5, 28.8, 31.6, 33.5, 33.9, 34.0, 35.1, 38.1, 39.8, 39.9, 40.8, 43.0, 43.1, 47.6, 47.9, 49.1, 56.7, 63.1, 68.1, 72.3, 75.6, 79.2, 79.7, 79.7, 124.7, 144.7, 180.7.

The chemical names of the above compounds Y9-Y16 were as follows:

Y9: 3-carbonyl-olean-12-en-28-oic acid-28-N-(2,3,4,6-tetra-O-acetyl-β-D-galactoside)
Y10: 3-carbonyl-olean-12-en-28-oic acid-28-N-(β-D-galactoside)
Y11: 3β,16α-dihydroxy-olean-12-en-28-oic acid-28-N-(2,3,4,6-tetra-O-acetyl-β-D-mannoside)
Y12: 3β,16α-dihydroxy-olean-12-en-28-oic acid-28-N-(β-D-mannoside)
Y13: 3β-hydroxy-urs-12-en-28-oic acid-28-N-(2,3,4,6-tetra-O-acetyl-(β-D-galactoside)
Y14: 3β-hydroxy-urs-12-en-28-oic acid-28-N-(β-D-galactoside)
Y15: 3β-hydroxy-urs-12-en-28-oic acid-28-N-(2,3,4,6-tetra-O-acetyl-β-D-mannoside)
Y16: 3β-hydroxy-urs-12-en-28-oic acid-28-N-(β-D-mannoside)

The identification data of parts of the compounds were as follows:

Y13: 3β-hydroxy-urs-12-en-28-oic acid-28-N-(2,3,4,6-tetra-O-acetyl-β-D-galactoside)

$^1$H NMR (400 MHz, CDCl3): δ 0.78, 0.80, 0.88, 0.93, 0.95, 0.99, 1.09, 2.00, 2.02, 2.05, 2.14 (11×CH3), 0.71-2.16 (m, other aliphatic ring protons), 3.21 (dd, 1H, J=5.0, 10.6 Hz), 3.97-4.09 (m, 3H), 5.02-5.16 (m, 3H), 5.41-5.42 (m, 2H), 6.61 (d, 1H, J=8.8Hz). 13C NMR (100 MHz, CDCl3): δ 15.4, 15.5, 17.0, 17.0, 18.1, 20.4, 20.5, 20.5, 20.7, 21.0, 23.0, 23.3, 24.8, 27.0, 27.7, 28.0, 30.7, 32.9, 36.8, 37.0, 38.6 (2C), 38.9, 39.4, 39.5, 42.2, 47.4, 47.8, 53.1, 55.1, 60.7, 67.0, 68.3, 70.7, 71.7, 78.6, 78.8, 126.2, 138.3, 169.7, 170.0, 170.2, 171.0, 178.6.

Y14: 3β-hydroxy-urs-12-en-28-oic acid-28-N-(β-D-galactoside)

$^1$H NMR (400 MHz, MeOD): δ0.78, 0.85, 0.91, 0.96, 0.97, 1.12 (7×CH3), 0.73-2.23 (m, other aliphatic ring protons), 3.15 (dd, 1H, J=4.8, 11.0 Hz), 3.49-3.66 (m, 5H), 3.89-3.90 (m, 1H), 4.77-4.82 (m, 1H), 5.31 (t, 1H, J=3.4 Hz), 7.44 (d, 1H, J=8.6). 13C NMR (100 MHz, MeOD): δ16.1, 16.4, 17.7, 18.1, 19.5, 21.6, 24.0, 24.4, 25.3, 27.9, 28.8, 29.0, 32.0, 34.3, 38.1, 38.3, 39.8, 40.1, 40.2, 40.8, 41.0, 43.3, 49.1, 54.0, 56.7, 62.2, 70.2, 71.3, 75.8, 77.9, 79.7, 81.9, 82.0, 127.3, 139.7, 181.4.

Experimental Examples

The experimental results of the anti-influenza virus of parts of the compounds according to the present invention were described as follows:

1. Q9 Effectively Inhibited the Replication of Influenza Virus.

CPE inhibition experiments and plaque formation reduction experiments showed that compound Q9 had significant inhibitory effect on influenza virus, more potent than positive drug ribavirin. CPE inhibition experiments showed that the $EC_{50}$ of compound Q9 against influenza viruses was 48.7 μM, while the $EC_{50}$ of positive drug Tamiflu (oseltamivir phosphate, OSV-P) was 45.6 μM, the $EC_{50}$ of ribavirin (RBV) was 42.7 μM (shown in Table 1). The plaque formation reduction experiments showed that the $IC_{50}$ of Q9 against influenza virus was <5 μM (as shown in FIG. 1). The $CC_{50}$ of Q9 in A549, MDCK and 293T cells were more than 100 μM. This showed that Q9 had almost no cytotoxicity.

TABLE 1

The activity of Q9 against influenza virus (WSN) and its cytotoxicity

|  |  | Q9 | Q10 | RBV | OSV-P |
|---|---|---|---|---|---|
| $CC_{50}$ (μM) | A549 | >100 | >100 | >100 | >100 |
|  | MDCK | >100 | >100 | >100 | >100 |
|  | 293T | >100 | >100 | >100 | >100 |
| $EC_{50}$ (μM) |  | 48.7 | >100 | 42.7 | 45.6 |

$^a$: $CC_{50}$, the concentration required to reduced normal, non infected cell viability by 50%.
$^b$: $EC_{50}$, the concentration required to reduced inhibition of viral infection-induced cytopathogenicity by 50%. The $EC_{50}$ of Q9 calculated by cytopathic effect (CPE) inhibition experiments was equivalent to the antiviral activity of ribavirin and oseltamivir phosphate, indicating that the anti-influenza virus effect of Q9 was similar to that of ribavirin and oseltamivir phosphate.

TABLE 2

Plaque formation reduction experiments showed that Q9 exhibited signification inhibitory effect on influenza virus.

| | Concentrations of Q9 | | | | | |
|---|---|---|---|---|---|---|
| | 100 μM | 50 μM | 25 μM | 10 μM | 5 μM | 0 μM |
| Plaque number | 0 | 7.6 ± 2.5 | 14.1 ± 1.7 | 21.8 ± 2.5 | 42.9 ± 5.8 | 100 |

The results showed that influenza virus could form virus plaques in MDCK cells and Q9 inhibited more than half of plaques at a concentration of 5 μM, i.e. $IC_{50}$<5 μM.

2. Q9 Inhibited Entry of Influenza Virus into Cells

The time-of-addition assays and hemagglutination inhibition assays above indicated that Q9 acted on the entry step of influenza virus into cells and interfered the binding of viruses to cellular receptors. (as shown in Table 3 and FIG. 1)

TABLE 3

Time-of-addition assay showed that Q9 acted on the early stage of viral replication (0-2 h)

| Time point | 0-10 h | 0-2 h | 2-5 h | 5-8 h | 8-10 h | DMSO |
|---|---|---|---|---|---|---|
| Viral NP level | 0.25 | 0.38 | 1.0 | 1.0 | 0.96 | 1.0 |

The results showed that the NP level at the interval 0-10 h and 0-2 h was reduced around 75% and 62%, respectively, as compared with the DMSO control. In contrast, no antiviral activity was detected for the remaining three intervals (2-5, 5-8, and 8-10 h). These data indicate that Q9 is effective at the early stage (0-2 h) of the viral lifecycle, No inhibitory effect was observed for the remaining steps, i.e., viral genome replication/translation and virion assembly/release.

3. Pseudotype Virus Experiments Showed that Q9 Inhibited Entry of H1N1 and H5N1 Influenza Strains into Cells.

Since H5N1 is highly pathogenic influenza virus, pseudotype viruses of H5N1 and H1N1 were used to measure the broad-spectrum of the antiviral activity of Q9. Such pseudotype viruses had highly security and can be operated in P2 laboratory. When the concentration was 50 μM, Q9 exhibited significant anti-viral activity against flu virus H1N1 and H5N1, with an inhibition rate of 61.9% and 16.8%, respectively. The higher the inhibition rate, the weaker the relative luciferase activity detected.

TABLE 4

Pseudotype virus experiments showed that Q9 inhibited pseudotype viruses of H1N1 and H5N1 influenza viruses.

| virus | compound | |
|---|---|---|
| | Q9 | DMSO |
| H1N1pp | 61.9 | 0 |
| H5N1pp | 16.8 | 0 |
| VSVpp | 3.8 | 0 |

Pseudotype virus was composed of the core portion of HIV and the envelope protein HA/NA of influenza virus. Two subtypes of influenza virus-H1N1 and H5N1 pseudotype viruses were inhibited by Q9; the concentration of Q9 was 50 μM. The inhibition rate of DMSO as a negative control was set to zero.

4. Anti-Influenza Viral Activity of Part of Sugar-Modified Triterpenoids Derivatives The compound was mixed with the virus and then added to the cells. The inhibitory effect of the compound on the virus-induced cytopathy effect was observed. The group only comprising the compound without viruses was used to measure the cytotoxicity of compounds. DMSO was used as a negative control. Canine kidney epithelial cells (MDCK) seeded and incubated for 24 h. The compound to be tested was added to DMEM, mixed uniformly and added to MDCK cells. 48 hours later, the cell viability was detected using Celltiter-Glo test kit. The results showed that Q9 had significant inhibition activity against influenza virus and significantly impaired viral infectivity; EA, Q1, Q2, Q3, Q11 and Q12 also exhibited some anti-influenza virus activity; the other compounds had no significant anti-influenza virus activity. In the compounds tested, EA, Q4 and Q6 had obvious cytotoxicity; the anti-influenza viral activity of Q1, Q2, Q3, Q11 and Q12 was not significant as compared to Q9, but had significantly reduced cytotoxivity as compared with EA. The other compounds exhibited very weak toxicity (As shown in Tables 5 and 6).

TABLE 5

Toxicity of each compound on MDCK cells at a concentration of 50 μM

| Compound | EA | Q1 | Q2 | Q3 | Q4 | Q5 | Q6 | Q8 |
|---|---|---|---|---|---|---|---|---|
| Cell viability(%) | 73.5 | 110.2 | 101.1 | 100.4 | 0.1 | 100.9 | 38.4 | 102.6 |

| Compound | Q9 | Q10 | Q11 | Q12 | Q13 | Q14 | DMSO |
|---|---|---|---|---|---|---|---|
| Cell viability(%) | 89 | 98.1 | 92.8 | 93.3 | 91.7 | 98.3 | 100 |

TABLE 6

Anti-influenza virus activity of compounds at a concentration of 50 μM. Lower viral infectivity represented better inhibitory effect of drugs. The detection method was shown as Table 5.

| Compound | EA | Q1 | Q2 | Q3 | Q5 | Q8 | Q9 |
|---|---|---|---|---|---|---|---|
| Viral Infectivity (%) | 67.9 | 78.7 | 76.2 | 71.1 | 107.5 | 109.7 | 21.1 |

| Compound | Q10 | Q11 | Q12 | Q13 | Q14 | DMSO |
|---|---|---|---|---|---|---|
| Viral Infectivity (%) | 100.6 | 82.6 | 80.1 | 115.5 | 154.4 | 100.0 |

DMSO was used as a negative control. After the canine kidney epithelial cells (MDCK) passaged 24 h, WSN virus (MOI=1) and the compound to be tested were added to DMEM, mixed uniformly and added to MDCK cells. 48 h later, the cell viability was detected using Celltiter-Glo assay kit. Infection rate (Infectivity)=100%-protective rate of a compound against cytopathy. Protective rate of a compound against cytopathy=100%×(1−(Test compound-Median Virus 1)/(Median Cells-Median Virus2)). In which Test compound represents the cell viability of the group to which only test compound was added without viruses; Median Virus1 represents the cell viability of the group to which test compound and viruses were added; Median Cells represents the cell viability of the group to which only 1% DMSO was added; Median Virus2 represents the cell viability of the group to which 1% DMSO and viruses were added.

Further structural modification on Q9 has shown that Y1, Y2, Y3, Y5, Y6, Y7 and Y8 have significant anti-influenza virus activity and weak cytotoxicity. In which Y5 exhibited most significant anti-influenza virus activity (as shown in Tables 7 and 8).

TABLE 7

Toxicity of compounds to MDCK cells at a concentration of 50 μM

| | Compound | | | | |
|---|---|---|---|---|---|
| | Y1 | Y2 | Y3 | Y4 | Y5 |
| Cell viability (%) | 84.8 | 105.0 | 80.8 | 98.5 | 81.7 |

| | Compound | | | | |
|---|---|---|---|---|---|
| | Y6 | Y7 | Y8 | Q9 | DMSO |
| Cell viability (%) | 98.7 | 82.3 | 85.0 | 100.3 | 100.0 |

TABLE 8

Anti-influenza virus activity of compounds at a concentration of 50 μM. Lower viral infectivity represented better inhibitory effect of drugs. The detection method was shown as Table 6.

| | Compound | | | | |
|---|---|---|---|---|---|
| | Y1 | Y2 | Y3 | Y4 | Y5 |
| Viral infectivity (%) | 16.4 | 17.5 | 16.3 | 31.1 | 9.0 |

TABLE 8-continued

Anti-influenza virus activity of compounds at a concentration of 50 μM. Lower viral infectivity represented better inhibitory effect of drugs. The detection method was shown as Table 6.

| | Compound | | | | |
|---|---|---|---|---|---|
| | Y6 | Y7 | Y8 | Q9 | DMSO |
| Viral infectivity (%) | 16.0 | 17.4 | 19.5 | 21.1 | 100 |

Further structural modification has shown that Y13 and Y14 have significant anti-influenza virus activity higher than Q9 and weak cytotoxicity (the data not shown). The other compounds also showed good anti-influenza virus activity (as shown in Table 9).

TABLE 9

Anti-influenza virus activity of compounds at a concentration of 50 μM. The detection method was shown as Table 6.

| Compound | IAV inhibition rate (%) |
|---|---|
| Y13 | 76.86 ± 5.53 |
| Y14 | 62.23 ± 2.96 |
| Q9 | 53.62 ± 6.16 |
| Y16 | 48.20 ± 4.22 |
| Y15 | 39.82 ± 3.60 |
| Y9 | 32.17 ± 1.81 |
| Y11 | 26.82 ± 3.46 |
| Y10 | 4.84 ± 3.08 |
| DMSO | 0.00 ± 0.00 |

Inhibition rate(%): protective rate of compounds against cytopathy. Calculation method was shown as Table 6.

5. The Experimental Results of the Anti-Influenza Viruses of Compounds were Shown as Follows:

The inhibition effect of compounds on different influenza viruses was tested through cytopathic effect (CPE) reduction assays. It was found that compounds Y2, Y5, Y6 and Q9 exhibited various extent of inhibition effect on A/Puerto Rico/8/34(H1N1): A/LiaoNing-ZhenXing/1109/2010 (H1N1): A/JiangXi-DongHu/312/2006 (H3N2): A/HuNan-ZhuHui/1222/2010 (H3N2): B/ShenZhen/155/2005. In which the $EC_{50}$ of Y5 was lower than 2 μM, equivalent to ribavirin. These strains include Tamiflu- and Amantadine-resistant strains; A/LiaoNing-ZhenXing/1109/2010(H1N1) is a Tamiflu-resistant strain; A/HuNan-ZhuHui/1222/2010 (H3N2) is an Amantadine-resistant strain. This showed that the compounds discovered by us can inhibit not only influenza A virus but also influenza B virus, indicating that they have broad-spectrum antiviral effect. Moreover, our compounds have significant inhibition effect on Tamiflu- and Amantadine-resistant strains (as shown in Table 10).

TABLE 10

Analytic results of broad-spectrum antiviral activity of compounds

| | | $EC_{50}$ (μM)[b] | | | | |
|---|---|---|---|---|---|---|
| Compound | $CC_{50}$ (μM)[a] | PR/8 (H1N1)[c] | LN/1109 (H1N1) | JX/312 (H3N2) | HN/1222 (H3N2) | B/SZ/155 |
| Y2 | >100 | 6.22 ± 0.83 | >22.22 | >22.22 | >22.22 | >22.22 |
| Y5 | >100 | 7.41 ± 0.05 | 6.58 ± 1.17 | 2.72 ± 0.35 | 3.18 ± 0.08 | 2.80 ± 0.74 |
| Y6 | >200 | 9.33 ± 0.60 | 33.25 ± 0.64 | 66.67 ± 0.17 | 26.25 ± 3.01 | 43.88 ± 19.38 |
| Q9 | >200 | 17.50 ± 0.43 | 17.80 ± 12.57 | 16.89 ± 5.38 | 25.59 ± 9.14 | 36.21 ± 7.21 |
| Amantadine | >200 | 7.41 ± 0.21 | 0.44 ± 0.14 | 8.58 ± 1.65 | >200 | >83.24 |
| Tamiflu | >200 | >200 | >200 | 2.06 ± 0.58 | 8.75 ± 4.41 | 91.07 ± 34.51 |
| Ribavirin | >200 | 4.02 ± 1.27 | 5.75 ± 0.35 | 4.19 ± 0.35 | 3.56 ± 0.24 | 1.32 ± 0.60 |

[a]$CC_{50}$, the concentration required to reduced normal, noninfected cell viability by 50%.
[b]$EC_{50}$, the concentration required to reduced inhibition of viral infection-induced cytopathogenicity by 50%. The $EC_{50}$ of Q9 was calculated by cytopathy effect inhibition experiments.
[c] PR/8 (H1N1), A/Puerto Rico/8/34 (H1N1); LN/1109(H1N1), A/LiaoNing-ZhenXing/1109/2010(H1N1); JX/312 (H3N2), A/JiangXi-DongHu/312/2006 (H3N2); HN/1222 (H3N2), A/HuNan-ZhuHui/1222/2010 (H3N2); B/SZ/155, B/ShenZhen/155/2005.

The present invention is not limited to the above embodiments. The above-described embodiments are merely illustrative and not restrictive. Under the inspiration of the present invention, those skilled in the art can make a lot of forms without departing from the spirit of the present invention and the protection scope claimed in the claims of the present invention, which forms all fall in the protection scope of the present invention.

The invention claimed is:

1. A method for treating influenza comprising administering to a subject in need thereof a compound of the following structural formula:

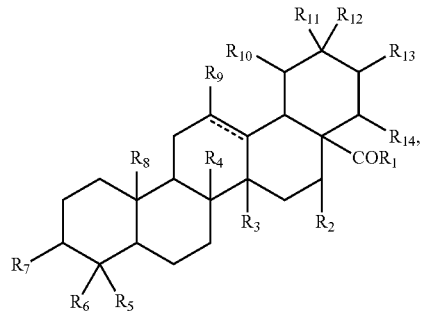

or a stereoisomer, an epimer, a configurational isomer, a pharmaceutically acceptable salt, or a hydrate thereof;
wherein:
the dotted line represents a single or double bond;
$R_1$ is $XR_1'$, wherein X is NH;
$R_1'$ is hydrogen, or
a monosaccharide, oligosaccharide, polysaccharide, a substituted monosaccharide, a substituted oligosaccharide, or a substituted polysaccharide, wherein the substituted monosaccharide, oligosaccharide, or polysaccharide has one, two, three or four hydroxyl groups each independently replaced with a substituent group selected from acetoxy, C1-C6 alkanoyloxy, C1-C6 alkoxy, benzoyloxy, benzyloxy, hydrogen, methoxy, an amino group, and an acetylamino group; or vitamin C, sialic acid, an amino sugar having one, two or three monosaccharide units, or Oseltamivir or a prodrug thereof;

$R_2$ and $R_7$ are each independently selected from the group consisting of H, halogen, hydroxy, cyano, nitro, mercapto, carbonyl, C1-C6 thioalkyl, C1-C6 alkyl group unsubstituted or substituted by a hydroxyl group, an amino group or a carboxyl group, amino, and $NR_{11}'R_{12}'$, wherein $R_{11}'$ and $R_{12}'$ are each independently selected from C1-C6 alkyl group unsubstituted or substituted by a hydroxyl group, an amino group or a carboxyl group;

$R_3$, $R_4$, $R_5$, $R_6$ and $R_8$ are each independently selected from the group consisting of H, C1-C6 alkyl group unsubstituted or substituted by a hydroxyl group, an amino group or a carboxyl group;

$R_9$ is selected from the group consisting of H, halogen, hydroxy, cyano, nitro, mercapto, C1-C6 thioalkyl group, a carbonyl group, an oxime group, C1-C6 alkyl group unsubstituted or substituted by a hydroxyl group, an amino group or a carboxyl group;

$R_{10}$, $R_{11}$, $R_{12}$, $R_{13}$ and $R_{14}$ are each independently selected from the group consisting of H, OH, $NHR_9'$, mercapto, C1-C6 thioalkyl, C1-C3 alkyl unsubstituted or substituted by hydroxyl, amino or carboxyl; and $R_9'$ is H, C1-C3 alkyl unsubstituted or substituted by hydroxyl, amino or carboxyl group, provided that when $R_7$ is hydroxyl, $R_2$ and $R_1'$ are not hydrogen.

2. The method according to claim 1, wherein $R_{10}$, $R_{11}$, $R_{12}$, $R_{13}$, and $R_{14}$ are each independently selected from the group consisting of H, hydroxy, amino, unsubstituted C1-C3 alkyl group; or $R_{10}$, $R_{11}$, $R_{12}$, $R_{13}$, and $R_{14}$ are each independently methyl or C1-C3 alkyl group substituted by hydroxy, amino or carboxyl group; or $R_{10}$, $R_{11}$, $R_{12}$, $R_{13}$, and $R_{14}$ are each independently methyl; or $R_{11}$ and $R_{12}$ are each independently selected from H or methyl, $R_{10}$ is H, and/or $R_{13}$ and $R_{14}$ are each independently selected from H, OH or $NH_2$.

3. The method according to claim 1, wherein the compound is administered by oral, rectal, nasal, aerosol or particulate inhalation, or administered topically by buccal and sublingual, transdermal, vaginal, intravesical, intralesional and parenteral route; or administered as a spray for oral or nasal administration, or indoor or topical environment sterilization and disinfection.

4. The method according to claim 1, wherein the monosaccharide is independently selected from the group consisting of glucose, mannose, fructose, xylose, arabinose, galactose, ribose and deoxyribose, wherein the oligosaccharide is maltose, sucrose or lactose.

5. The method according to claim 1, wherein:
X is NH;
$R_1'$ is a monosaccharide or disaccharide, or an acetylated derivative, wherein a hydroxyl group of the monosaccharide or disaccharide is replaced with an acetoxy group.

6. The method according to claim 1, wherein $R_2$ is H, OH, carbonyl, SH or $NH_2$, or wherein $R_2$ is H, OH or carbonyl.

7. The method according to claim 1, wherein $R_3$, $R_4$, $R_5$, $R_6$ and $R_8$ are each methyl.

8. The method according to claim 1, wherein $R_7$ is independently selected from the group consisting of H, OH, carbonyl, $NH_2$ or SH, or wherein $R_7$ is OH or carbonyl.

9. The method according to claim 1, wherein the compound is:
any one of compounds Y1-Y16,
3β,16α-dihydroxy-olean-12-en-28-oic acid-28-N-(2,3,4,6-tetra-O-acetyl-β-D-galactoside),
3β,16α-dihydroxy-olean-12-en-28-oic acid-28-N-(β-D-galactoside),
3,16-dione-olean-12-en-28-oic acid-28-N-(2,3,4,6-tetra-O-acetyl-β-D-galactoside),
3,16-dione-olean-12-en-28-oic acid-28-N-(β-D-galactoside),
3β-hydroxy-olean-12-en-28-oic acid-28-N-(2,3,4,6-tetra-O-acetyl-β-D-galactoside),
3β-hydroxy-olean-12-en-28-oic acid-28-N-(β-D-galactoside),
3β-hydroxy-olean-12-en-28-oic acid-28-N-(2,3,4,6-tetra-O-acetyl-β-D-mannoside),
3β-hydroxy-olean-12-en-28-oic acid-28-N-(β-D-galactoside),
3-carbonyl-olean-12-en-28-oic acid-28-N-(2,3,4,6-tetra-O-acetyl-β-D-galactoside),
3-carbonyl-olean-12-en-28-oic acid-28-N-(Jβ-D-galactoside),
3β,16α-dihydroxy-olean-12-en-28-oic acid-28-N-(2,3,4,6-tetra-O-acetyl-β-D-mannoside),
3β,16α-dihydroxy-olean-12-en-28-oic acid-28-N-β-D-galactoside),
3β-hydroxy-urs-12-en-28-oic acid-28-N-(2,3,4,6-tetra-O-acetyl-β-D-galactoside),
3β-hydroxy-urs-12-en-28-oic acid-28-N-(β-D-galactoside),
3β-hydroxy-urs-12-en-28-oic acid-28-N-(2,3,4,6-tetra-O-acetyl-(β-D-mannoside), and
3β-hydroxy-urs-12-en-28-oic acid-28-N-(β-D-mannoside).

10. The method according to claim 1, wherein the benzene ring of the benzoyloxy or benzyloxy group of the substituted monosaccharide, oligosaccharide, or polysaccharide is unsubstituted or substituted with one or more groups selected from halogen, nitro, amino and C1-C6 alkyl.

11. The method according to claim 1, wherein the compound inhibits influenza virus infection.

12. The method according to claim 1, wherein:
X is NH;
$R_1'$ is an acetylated galactose derivative in which a hydroxy group is replaced with an acetoxy group.

13. The method of claim 1, wherein the compound is

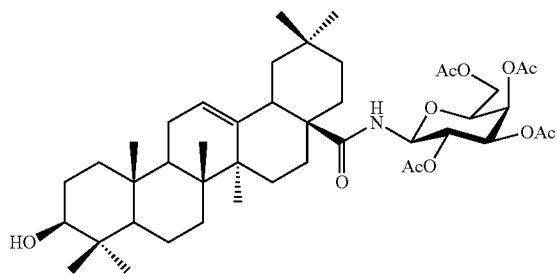

or a stereoisomer, an epimer, a configurational isomer, a pharmaceutically acceptable salt, or a hydrate thereof.

* * * * *